(12) United States Patent
Ferraro et al.

(10) Patent No.: US 9,447,326 B2
(45) Date of Patent: Sep. 20, 2016

(54) PRETREATMENT OF BIOMASS USING STEAM EXPLOSION METHODS BEFORE GASIFICATION

(71) Applicant: Sundrop Fuels, Inc., Longmont, CO (US)

(72) Inventors: Francis Michael Ferraro, Westminster, CO (US); Jerrod Wayne Hohman, Louisville, CO (US); Robert S. Ampulski, Fairfield, OH (US)

(73) Assignee: Sundrop Fuels, Inc., Longmont, CO (US)

( * ) Notice: Subject to any disclaimer, the term of this patent is extended or adjusted under 35 U.S.C. 154(b) by 167 days.

(21) Appl. No.: 14/276,719

(22) Filed: May 13, 2014

(65) Prior Publication Data

US 2014/0249237 A1  Sep. 4, 2014

Related U.S. Application Data

(63) Continuation-in-part of application No. 13/531,318, filed on Jun. 22, 2012, now Pat. No. 8,961,628, and a continuation-in-part of application No. PCT/US2013/044143, filed on Jun. 4, 2013, which is a continuation-in-part of application No. 13/531,318.

(60) Provisional application No. 61/823,360, filed on May 14, 2013.

(51) Int. Cl.
*B01J 7/00* (2006.01)
*C10B 49/02* (2006.01)
(Continued)

(52) U.S. Cl.
CPC .............. *C10B 49/02* (2013.01); *B01J 8/0025* (2013.01); *B01J 8/087* (2013.01); *B01J 8/12* (2013.01); *B01J 19/02* (2013.01); *C07C 29/1518* (2013.01);
(Continued)

(58) Field of Classification Search
CPC ................... C10J 2300/0906; C10J 2200/09; C10J 3/723
See application file for complete search history.

(56) References Cited

U.S. PATENT DOCUMENTS 5,196,460 A  3/1993  Lora et al.
5,747,320 A  5/1998  Saha et al.
(Continued)

FOREIGN PATENT DOCUMENTS

WO   WO 2011/159154 A1   12/2011

OTHER PUBLICATIONS

U.S. Appl. No. 61/119,062, filed Dec. 2, 2008, Stites.
(Continued)

*Primary Examiner* — Imran Akram
(74) *Attorney, Agent, or Firm* — Rutan & Tucker, LLP

(57) ABSTRACT

An integrated plant that includes a steam explosion process unit and biomass gasifier to generate syngas from biomass is discussed. A steam explosion process unit applies a combination of heat, pressure, and moisture to the biomass to make the biomass into a moist fine particle form. The steam explosion process unit applies steam with a high pressure to heat and pressurize any gases and fluids present inside the biomass to internally blow apart the bulk structure of the biomass via a rapid depressurization of the biomass with the increased moisture content. Those produced moist fine particles of biomass are subsequently fed to a feed section of the biomass gasifier, which reacts the biomass particles in a rapid biomass gasification reaction to produce syngas components.

11 Claims, 13 Drawing Sheets

(51) Int. Cl.

| | | |
|---|---|---|
| *C07C 29/151* | (2006.01) | |
| *C10J 3/48* | (2006.01) | |
| *C10K 3/02* | (2006.01) | |
| *C10L 9/08* | (2006.01) | |
| *D21C 1/02* | (2006.01) | |
| *B01J 8/08* | (2006.01) | |
| *B01J 8/12* | (2006.01) | |
| *B01J 19/02* | (2006.01) | |
| *B01J 8/00* | (2006.01) | |
| *C10G 2/00* | (2006.01) | |

(52) U.S. Cl.
CPC .................. *C10G 2/32* (2013.01); *C10J 3/485* (2013.01); *C10K 3/02* (2013.01); *C10L 9/083* (2013.01); *D21C 1/02* (2013.01); *B01J 2208/0084* (2013.01); *B01J 2208/00123* (2013.01); *B01J 2208/00132* (2013.01); *B01J 2208/00504* (2013.01); *B01J 2208/00513* (2013.01); *B01J 2219/0263* (2013.01); *C10G 2300/1014* (2013.01); *C10J 2300/092* (2013.01); *C10J 2300/0906* (2013.01); *C10J 2300/0909* (2013.01); *C10J 2300/0916* (2013.01); *C10J 2300/0976* (2013.01); *C10J 2300/1223* (2013.01); *C10J 2300/1665* (2013.01); *C10J 2300/1853* (2013.01); *Y02E 50/15* (2013.01); *Y02E 50/18* (2013.01); *Y02P 20/145* (2015.11); *Y02P 30/20* (2015.11)

(56) References Cited

U.S. PATENT DOCUMENTS

| | | | |
|---|---|---|---|
| 5,769,934 | A | 6/1998 | Ha et al. |
| 5,882,905 | A | 3/1999 | Saha et al. |
| 6,172,204 | B1 | 1/2001 | Sarkanen et al. |
| 6,555,350 | B2 | 4/2003 | Ahring et al. |
| 6,660,506 | B2 | 12/2003 | Nguyen et al. |
| 6,899,791 | B2 | 5/2005 | Sabourin |
| 7,109,005 | B2 | 9/2006 | Eroma et al. |
| 7,300,540 | B2 | 11/2007 | Sabourin et al. |
| 7,625,728 | B2 | 12/2009 | Eroma et al. |
| 7,713,381 | B2 | 5/2010 | Sabourin et al. |
| 7,846,294 | B2 | 12/2010 | Sabourin et al. |
| 7,919,070 | B2 | 4/2011 | Stites et al. |
| 8,003,352 | B2 | 8/2011 | Foody et al. |
| 8,028,945 | B2 | 10/2011 | Gingras |
| 8,057,639 | B2 | 11/2011 | Pschorn et al. |
| 8,157,195 | B2 | 4/2012 | Gingras |
| 8,187,849 | B2 | 5/2012 | Larsen |
| 8,192,854 | B2 | 6/2012 | Borole |
| 8,378,151 | B2 | 2/2013 | Perkins et al. |
| 2009/0221814 | A1 | 9/2009 | Pschorn et al. |
| 2009/0286295 | A1 | 11/2009 | Medoff et al. |
| 2010/0068778 | A1 | 3/2010 | Chen et al. |
| 2010/0137459 | A1 | 6/2010 | Stites et al. |
| 2010/0237291 | A1 | 9/2010 | Simmons et al. |
| 2010/0270505 | A1 | 10/2010 | Gallaspy et al. |
| 2010/0273899 | A1 | 10/2010 | Winter |
| 2010/0317053 | A1 | 12/2010 | Stromberg et al. |
| 2011/0111456 | A1 | 5/2011 | Medoff |
| 2011/0126448 | A1 | 6/2011 | Dumenil |
| 2011/0150722 | A1 | 6/2011 | Stites et al. |
| 2012/0041186 | A1 | 2/2012 | Pschorn et al. |
| 2012/0047794 | A1 | 3/2012 | Bartek et al. |
| 2012/0060412 | A1 | 3/2012 | Raiko |
| 2012/0220005 | A1 | 8/2012 | Kumagai et al. |
| 2013/0115653 | A1 | 5/2013 | Peterson et al. |
| 2013/0143263 | A1 | 6/2013 | Christensen et al. |
| 2013/0228298 | A1 | 9/2013 | Balakshin et al. |
| 2013/0247454 | A1* | 9/2013 | Laska ...................... C07C 2/00 44/457 |
| 2013/0248767 | A1* | 9/2013 | Ampulski ................ B01J 8/087 252/373 |
| 2013/0256113 | A1 | 10/2013 | Tumiatti et al. |
| 2013/0341569 | A1 | 12/2013 | Ampulski et al. |

OTHER PUBLICATIONS

Higuchi, Takayoshi "Steam Explosion of Wood", Sections 1-4, Biomass Handbook, © 1989 by OPA (Amsterdam), pp. 470-473 plus Cover, Biblio, Table of Contents excerpt. 7 pages total, Editors: Osamu Kitani & Carl W. Hall, ISBN 2-88124-269-3, Gordon and Breach Science Publishers S. A., Cooper Station, New York, New York.

"StakeTech—First Pulping System Receives Full Acceptance", May 14, 1996, 2 pages Publisher: Business Wire. downloaded from http://www.thefreelibrary.com/StakeTech.

McCallum, Don, "Medium Density Fiber Board" pp. 8-11, Nov. 1, 1996 http://fennerschool-associated.anu.edu.au/fpt/mdf/manufacture.html.

Lam, PS, "Steam Explosion of Biomass to Produce Durable Wood Pellets", The University of British Columbia, May 2011, Retrieved from the Internet on Oct. 21, 2013 from URL https://circle.ubc.ca/bitstream/id/123471/ubs_2011_fall_Iam_paksui.pdf. p. 33, Paragraph 1; p. 43, Paragraphs 1-3, Tables 2.4-2.5.

International Search Report and Written Opinion for International Application No. PCT/US2013/044143 mailed Nov. 13, 2013, 18 pages. International Searching Authority/US, Alexandria, Virginia USA.

Non Final Rejection Action for U.S. Appl. No. 13/531,318 mailed Oct. 25, 2013, 6 pages. International Searching Authority/US, Alexandria, Virginia USA.

Restriction Requirement for U.S. Appl. No. 13/531,318 mailed May 20, 2013, 7 pages. International Searching Authority/US, Alexandria, Virginia USA.

Final Office Action for U.S. Appl. No. 13/531,318 mailed May 29, 2014, 7 pgs. International Searching Authority/US, Alexandria, Virginia USA.

* cited by examiner

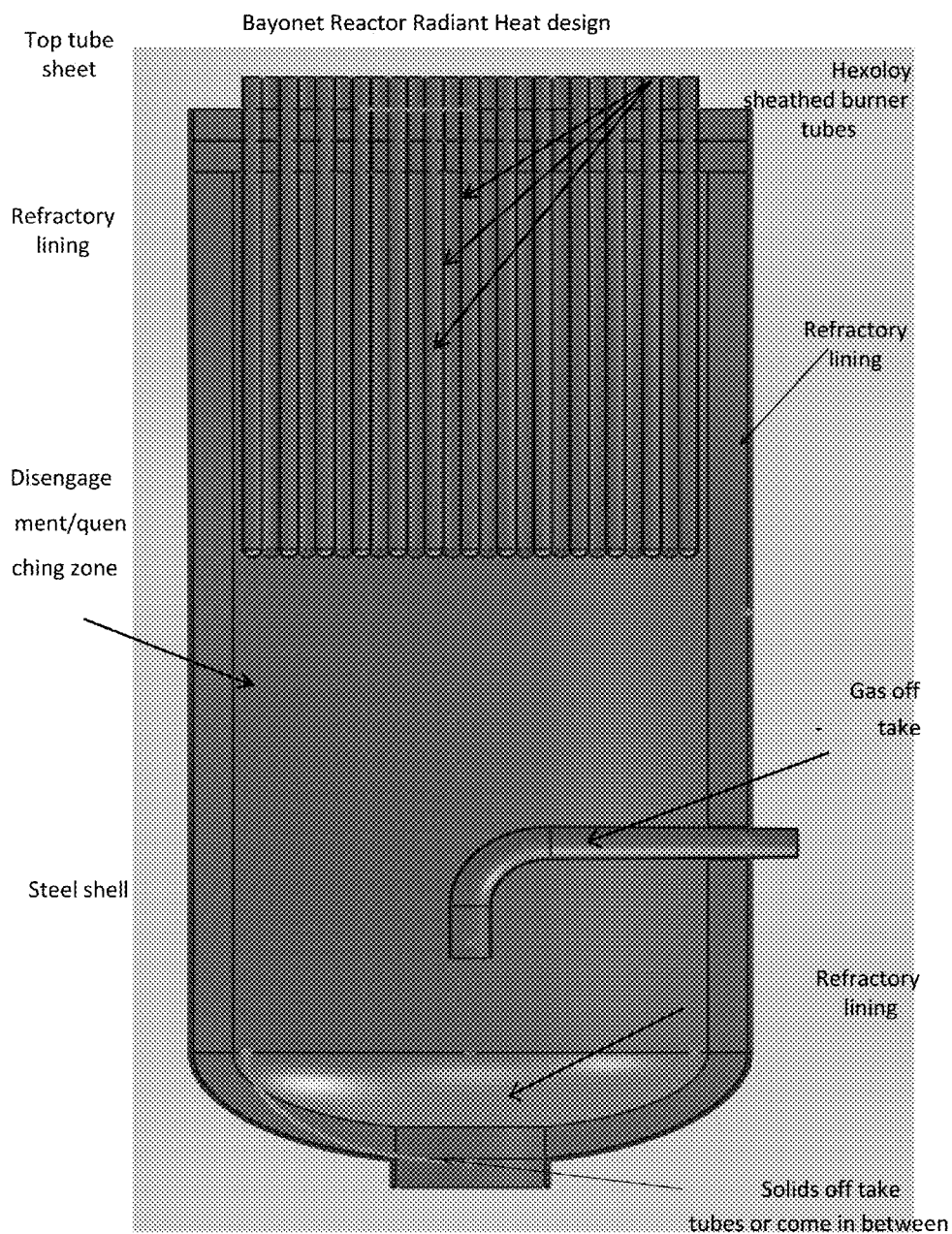
Biomass lines can either be between SiC tube sheet and refractory
Integral spray quench (below SiC tubes) is optional          Figure 3-3

PRETREATMENT OF BIOMASS USING STEAM EXPLOSION METHODS BEFORE GASIFICATION

RELATED APPLICATIONS

This application claims priority to and the benefit as a Continuation in Part of U.S. Non-Provisional application Ser. No. 13/531,318 titled "Pretreatment of Biomass Using Steam Explosion Methods Before Gasification," filed 22 Jun. 2012 as a Continuation In Part Application. This Application also claims priority to and the benefit of U.S. Provisional Application No. 61/823,360 titled "Pretreatment of Biomass Using Steam Explosion Methods Before Gasification," filed 14 May 2013 under 35 U.S.C. §119. This Application also claims priority to and the benefit as a Continuation in Part of PCT application number PCT/US13/44143, titled "Pretreatment of Biomass Using Steam Explosion Methods Before Gasification," dated Jun. 4, 2013, which was an international filing that claimed priority to and the benefit of the above U.S. Provisional Application No. 61/823,360 and U.S. Non-Provisional application Ser. No. 13/531,318; of which all three Applications are hereby incorporated by reference.

FIELD

The design generally relates to treatment of biomass using steam explosion methods as a pre-process before gasification or combustion. In an embodiment, the design specifically relates to an integrated plant that uses this biomass to produce a liquid fuel from the biomass or to convert the biomass into a densified form to facilitate economic transport to facilities for further processing to liquid fuel, heat/power, animal feed, bedding, or chemicals.

BACKGROUND

The technology was originally conceived to make medium density fiberboard with dry wood chips. Other processes require multiple steps of grinding the wood chips, drying the chips, re-grinding the chips, moisturizing the fibers, densifying the fibers, and then densifying the wood chips (such as in the form of pellets). These processes are complex, capital intensive and require large amounts of energy. Some other typical processes need to dry the chips of biomass and then grind the chips to very small dimensions before sending them to a subsequent heating/processing unit. This drying and grinding takes a lot of energy and capital costs. These processes produce small fibers but ones that are many times the size of the fine particles produced by a Steam Explosion Process (SEP). Previous industries using a SEP process wish to maintain the integrity of the fiber making up biomass as well as the fiber strength; and thus, have longer fragments of that are not subjected to as severe conditions in a steam explosion unit. Also, additional mechanical agitation of the biomass is not applied as that would further reduce both fiber length and integrity.

SUMMARY

An integrated plant that includes a steam explosion unit and biomass gasifier to generate syngas from biomass. A steam explosion unit applies a combination of heat, pressure, and moisture to the biomass to make the biomass into a moist, fine particle form. The steam explosion unit applies steam with a high pressure to heat and pressurize any gases and fluids present inside the biomass. Where at an exit orifice to the two or more stages, a bulk structure of the pressurized biomass is internally blown apart to internally blow apart via a rapid depressurization of the biomass with the increased moisture content. Those produced moist, fine particles of biomass are subsequently fed to a feed section of the biomass gasifier, which reacts with the biomass particles in a rapid biomass gasification reaction to produce syngas components. The steam explosion stage of the steam explosion unit couples to a refiner stage that has one or more blades configured to mechanically agitate the biomass prior to the biomass exiting the steam explosion stage through an orifice to a blow line.

BRIEF DESCRIPTION OF THE DRAWINGS

The multiple drawings refer to the example embodiments of the design.

Figure 1A:
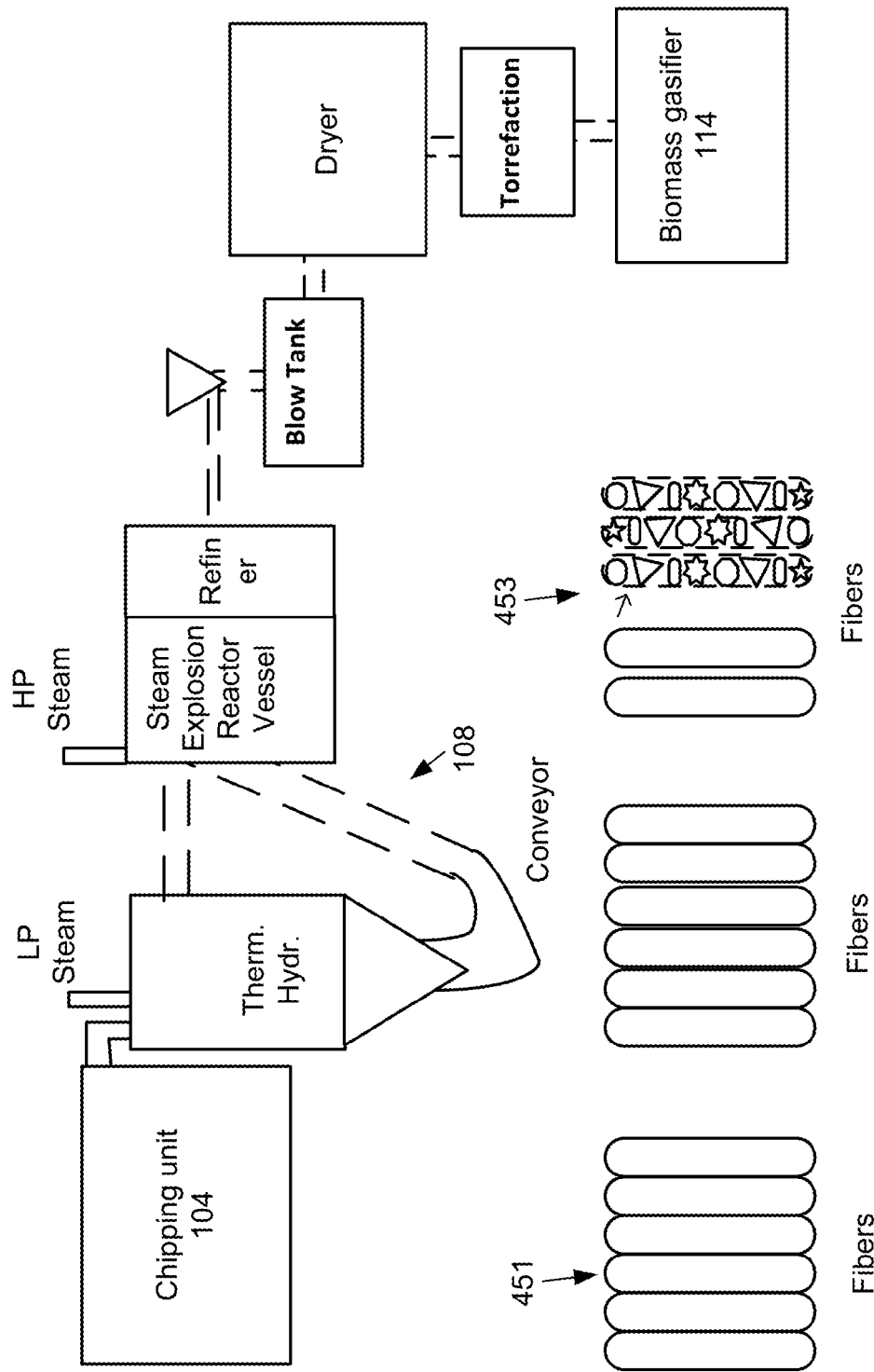
FIGS. 1A and 1B illustrate flow schematics of embodiments of a steam explosion unit having an input cavity to receive biomass as a feedstock, two or more steam supply inputs, and two or more stages to pre-treat the biomass for subsequent supply to a biomass gasifier.

While the design is subject to various modifications and alternative forms, specific embodiments thereof have been shown by way of example in the drawings and will be described in detail herein. The design should be understood to not be limited to the particular forms disclosed, but on the contrary, the intention is to cover all modifications, equivalents, and alternatives falling within the spirit and scope of the design.

DETAILED DISCUSSION

In the following description, numerous specific details are set forth, such as examples of specific chemicals, named components, connections, types of heat sources, etc., in order to provide a thorough understanding of the present design. It will be apparent, however, to one skilled in the art that the present design may be practiced without these specific details. In other instances, well known components or methods have not been described in detail but rather in a block diagram in order to avoid unnecessarily obscuring the present design. Thus, the specific details set forth are merely exemplary. The specific details may be varied from and still be contemplated to be within the spirit and scope of the present design.

In general, a number of example processes for and apparatuses associated with pre-treatments of biomass are described. The following drawings and text describe various example implementations for an integrated plant using the pre-treatments of biomass. In an embodiment, the integrated plant contains at least a steam explosion unit and a biomass gasifier to generate syngas from biomass. The steam explosion unit may have one or more input cavities to receive biomass as a feedstock, one or more steam supply inputs, and two or more stages to pre-treat the biomass to make particles of biomass for subsequent supply to the biomass gasifier. The stages use a combination of heat, pressure, and moisture that are applied to the biomass to make the biomass into a moist fine particle form. The steam explosion process breaks down a bulk structure of the received biomass, at least in part, by applying steam from a first steam supply input to begin degrading bonds between lignin and hemi-cellulose from cellulose fibers of the biomass and increase a moisture content of the received biomass. In the last stage, steam, at at least fourteen times atmospheric pressure, from a second steam supply input is applied to heat and pressurize any gases and fluids present inside the biomass. Where at an exit orifice from the two or more stages, a bulk structure of the pressurized biomass is internally blown apart. The bulk structure of the biomass is blown apart via a rapid depressurization of the biomass with the increased moisture content and degraded bonds. The biomass produced into the moist fine particle form from the stages may have average dimensions of, for example, less than 70 microns thick and less than 500 microns in length. Those produced moist fine particles of biomass are subsequently fed to a feed section of the biomass gasifier. The biomass gasifier has a reactor vessel configured to react the biomass in moist fine particle form with an increased surface area and decreased particle size compared to the received chips of biomass in the input cavity due to being blown apart by the steam explosion unit. The biomass gasifier has a third steam supply input and one or more heaters, and in the presence of the steam the biomass in fine particle form are reacted in the reactor vessel in a rapid biomass gasification reaction in between a 0.1 second to 300.0 second resident time to produce at least syngas components, including hydrogen ($H_2$) and carbon monoxide ($CO$).

A possible biomass gasifier implementation has a high temperature steam supply input and one or more heaters, such as, for example, gas fire burners or regenerative heaters. In the presence of the steam, the particles of the biomass broken down by the steam explosion unit are reacted in the reactor vessel in a rapid biomass gasification reaction at a temperature of greater than 700 degrees C. in less than a one second residence time in the biomass gasifier to create syngas components, including hydrogen ($H_2$) and carbon monoxide ($CO$), which are fed to a methanol ($CH_3OH$) synthesis reactor. One skilled in the art will understand parts and aspects of many of the designs discussed below within this illustrative document may be used as stand-alone concepts or in combination with each other.

Figure 1B:
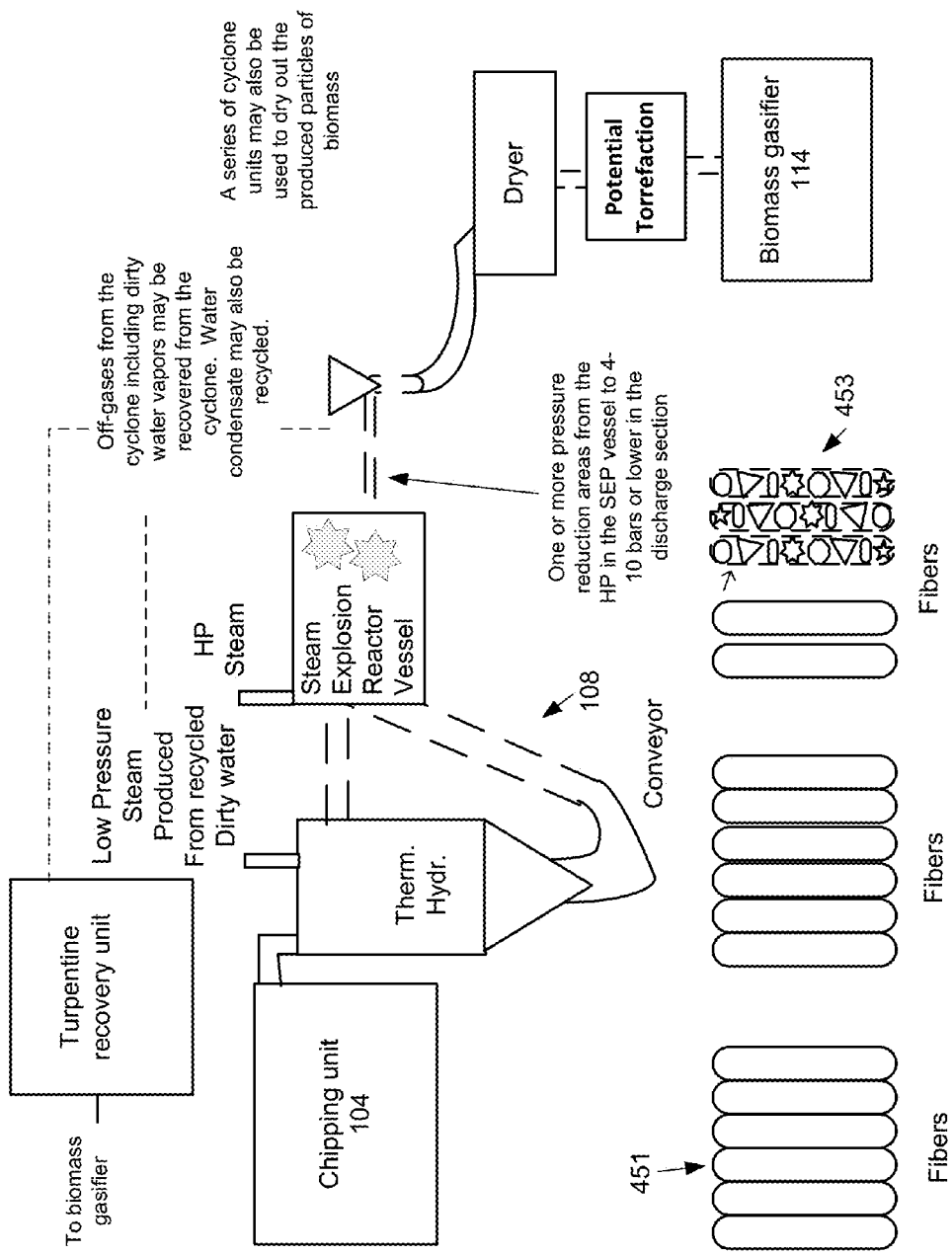

FIGS. 1A and 1B illustrate flow schematics of embodiments of a steam explosion unit having an input cavity to receive biomass as a feedstock, two or more steam supply inputs, and two or more stages to pre-treat the biomass for subsequent supply to a biomass gasifier.

Figure 4A:
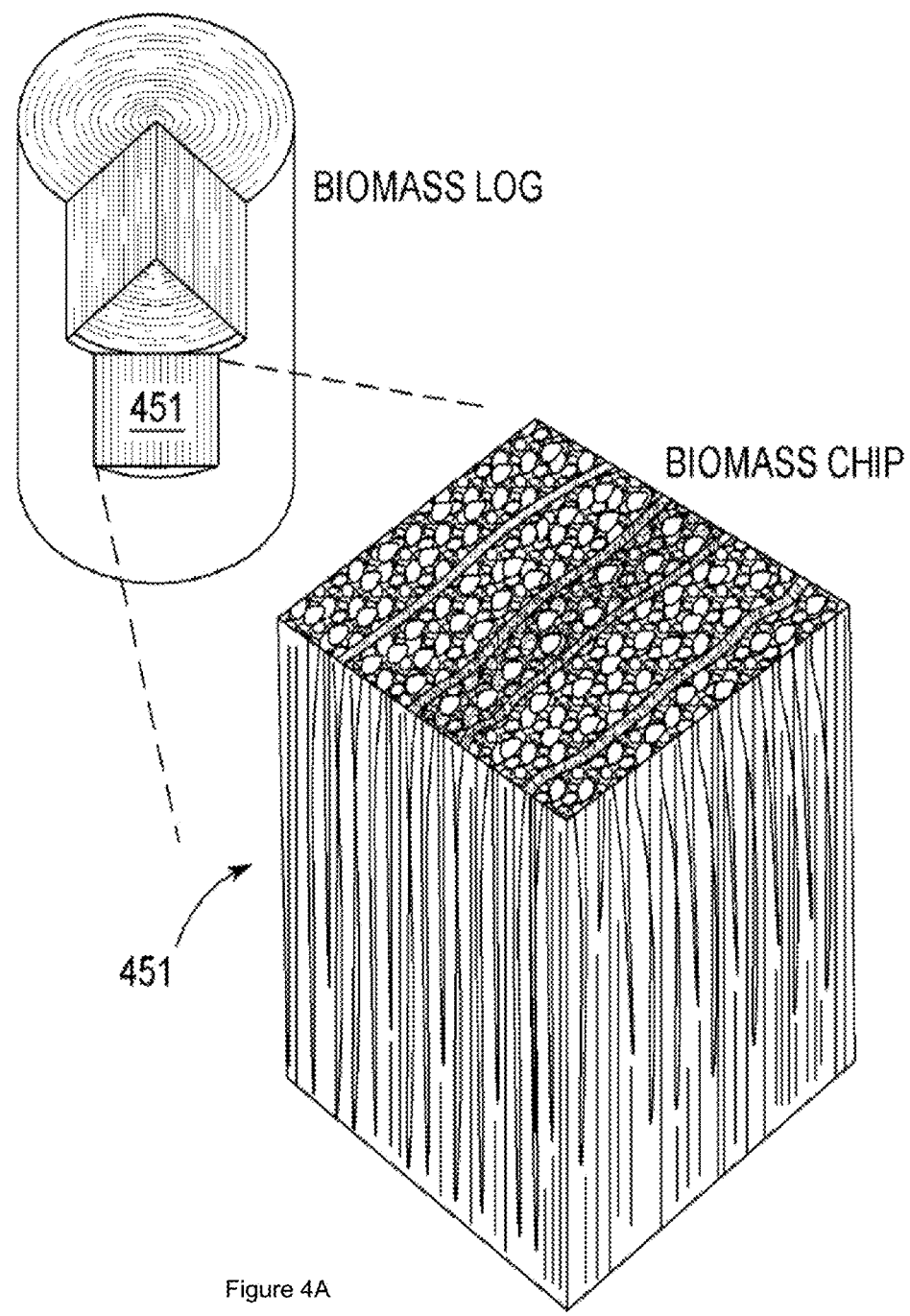
FIGS. 4A-C illustrate different levels of magnification of an example chip of biomass having a fiber bundle of cellulose fibers surrounded and bonded together by lignin.

Moisture values in the incoming biomass in chip form can vary from about 15% to 60% for biomass left outside without extra drying. Chips of biomass may be generated by a chipper unit 104 cooperating with some filters with dimensions to create chips of less than about one inch and on average about 0.5 inch in average length and a 0.25 inch in thickness on average. (See for example FIG. 4a illustrating a chip of biomass 451 from a log of biomass 453) The biomass chipper unit 104 may contain four or more blades used to chop and chip the biomass. The feed speed of the logs of biomass, the speed of the knife blades, the protrusion distance of the knives and the angle of the knives, can all act to control the chip size. The chips are then screened and those that are oversized may be rechipped. There may be a blending of chips from different sources or timber species to enhance certain properties. A magnet or other scanner may be passed over to detect and remove impurities. Chips of biomass are fed on a conveyor or potentially placed in a pressure vessel in the thermally decomposing stage in the steam explosion unit 108 that starts a decomposition, hydrating/moistening, and softening of the chips of biomass using initially low-pressure saturated steam. The low-pressure saturated steam may be at 100 degrees C. The system may also inject some flow aids at this point, such as recycled ash from the biomass gasifier 114, to prevent clogs and plugging by the biomass chips.

The chipper unit 104 may feed to and the steam explosion unit 108 is configured to receive two or more types of biomass feed stocks, where the different types of biomass include 1) soft woods, 2) hard woods, 3) grasses, 4) plant hulls, and 5) any combination that are blended and steam explosion processed into a homogenized torrefied feedstock within the steam explosion unit 108 that is subsequently collected and then fed into the biomass gasifier 114. The steam explosion unit 108, dryer 112, and biomass gasifier 114 are designed to be feedstock flexible without changing out the physical design of the feed supply equipment or the physical design of the biomass gasifier 114 via at least particle size control of the biomass particles produced from steam explosion stage and dryer 112. The dryer 112 may be a flash dryer, a drum dryer, a paddle dryer, air dryer, or similar such device.

As discussed, a magnetic filter and an air cleaning filter system may couple to the thermal hydrating stage to ensure metal fragments and heavy rocks are removed from the biomass in chip form prior to entering the thermal hydrating stage. The magnetic filter and the air cleaning filter system prevent any metal fragments and/or heavy rocks from plugging portions of the steam explosion unit including the discharge outlet. The air cleaning filter system assists in dropping out really heavy rocks as well as light weight sand. Note, the orifice forming the discharge outlet of the steam explosion stage may be, for example, 0.25 to 0.375 of an inch.

Figure 4B:
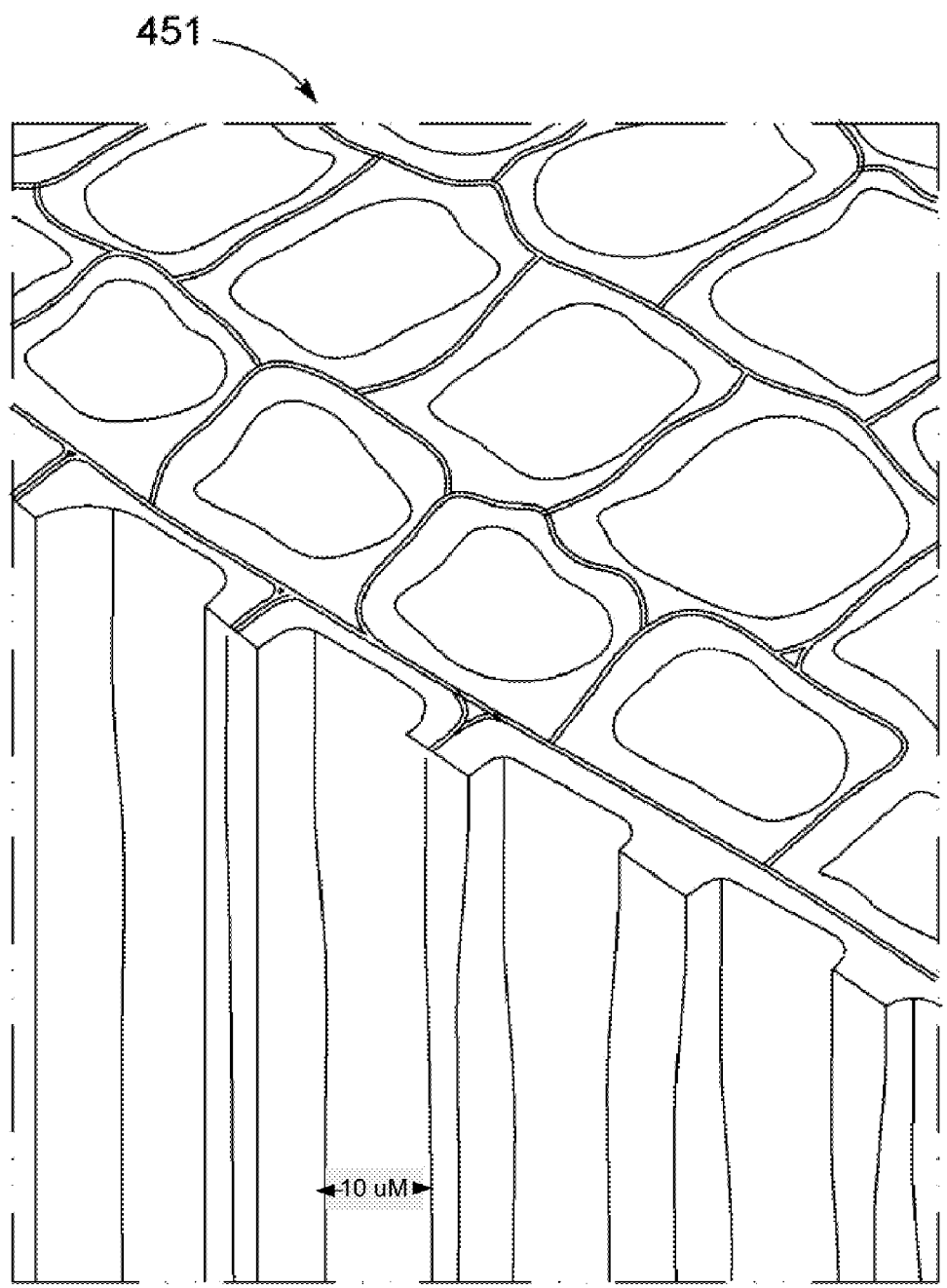

The steam explosion unit 108 has an input cavity to receive biomass as a feedstock, one or more steam supply inputs, and two or more stages to pre-treat the biomass for subsequent supply to a biomass gasifier 114. The stages use a combination of heat, pressure, and moisture that are applied to the biomass to make the biomass into a moist fine particle form. The steam explosion process breaks down a bulk structure of the received biomass, at least in part, by applying steam from a low pressure steam supply input to begin degrading bonds between lignin and hemi-cellulose from cellulose fibers of the biomass and increase a moisture content of the received biomass. (See for example FIG. 4B illustrating a chip of biomass having a fiber bundle of cellulose fibers surrounded and bonded together by lignin.) In the last stage, steam at at least fourteen times atmospheric pressure from a high pressure steam supply input is applied to heat and pressurize any gases and fluids present inside the biomass to internally blow apart the bulk structure of the received biomass via a rapid depressurization of the biomass with the increased moisture content and degraded bonds.

In an embodiment, the two or more stages of the steam explosion unit 108 include at least a thermal hydrating stage and a steam explosion stage.

The thermal hydrating stage has the input cavity to receive chips of the biomass and the low pressure steam supply input to apply low-pressure saturated steam into a vessel containing the chips of biomass. The thermal hydrating stage is configured to receive the biomass in chip form including leaves, needles, bark, and wood. The thermal hydrating stage applies the low-pressure steam to the biomass at a temperature above a glass transition point of the lignin in order to soften and elevate the moisture content the biomass so the cellulose fibers of the biomass in the steam explosion stage can easily be internally blown apart from the biomass in chip form. In an embodiment, the chips of biomass are heated to greater than 60° C. using the steam. The low pressure steam supply input applies low-pressure saturated steam into a vessel containing the chips of biomass at an elevated temperature of above 60 degrees C. but less than 145 degrees C at a pressure around atmospheric PSI, to start a decomposition, hydrating, and softening of the received biomass in chip form. The low pressure supply input may consist of several nozzles strategically placed around the vessel. A set of temperature sensors provides feedback on the elevated temperature of the received chips of biomass. A control system is configured to keep the chips of biomass to stay for a residence time of 8 to 20 minutes in the thermal hydrating stage, which is long enough to saturate the chips of biomass with moisture before moving out the biomass to the steam explosion stage. Shorter residence times exist for wood chunks from the trunk of the tree and longer residence times exist for tree limbs, tree needles, etc.

Figure 4C:
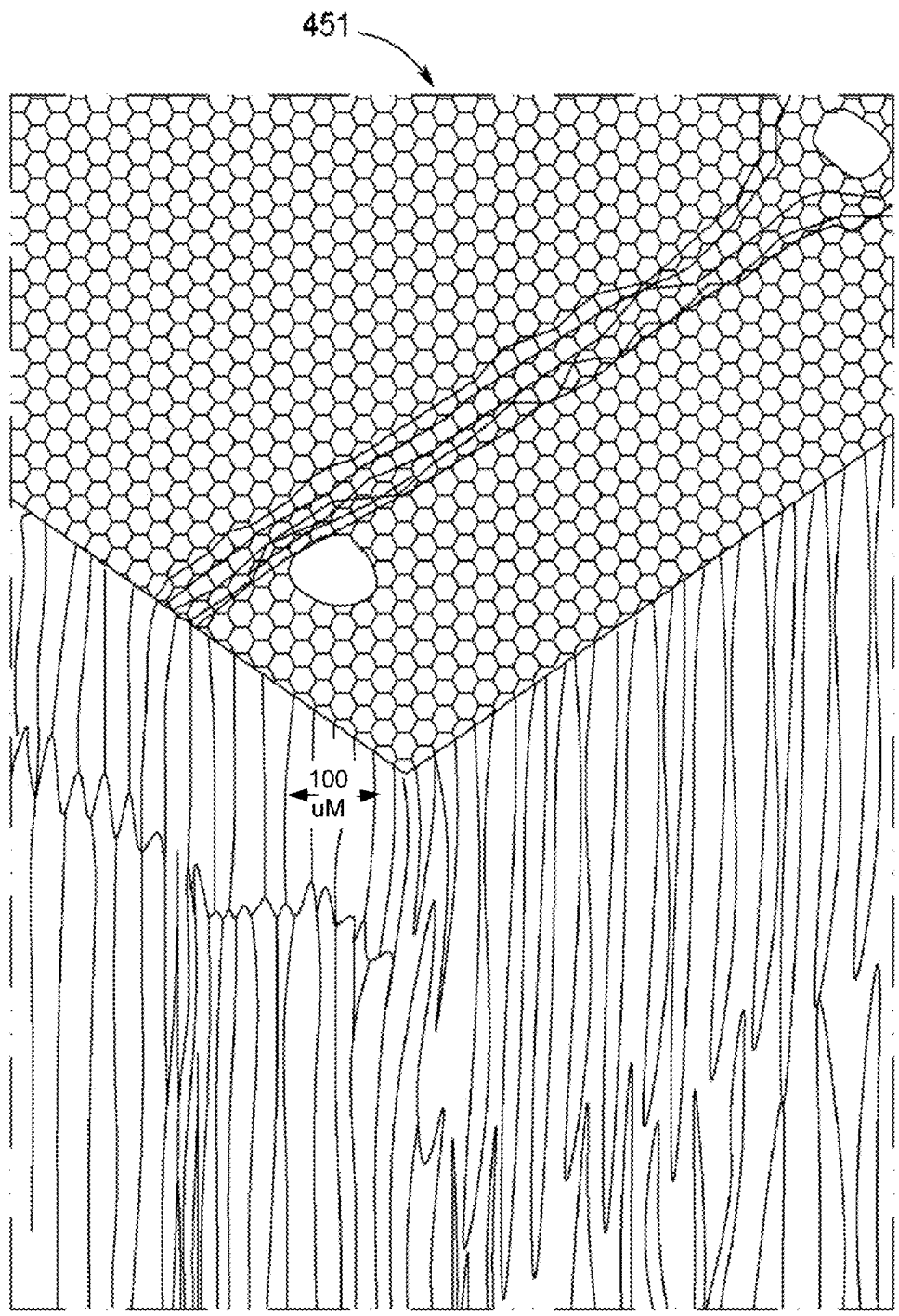

The thermal hydrating stage, potentially via a screw feed system, feeds chips of biomass that have been softened and increased in moisture content to the steam explosion stage. A control system maintains a pressure of the steam explosion stage to be 10 to 30 times greater than the pressure that is present in the thermal hydrating stage and at an elevated temperature, such as a temperature of 160-270° C., 190-220° C. preferably. The pressure may be at 180-450 Pound per Square Inch (PSI) (300 PSI preferably). The steam explosion stage further raises the moisture content of the biomass to at least 40% by weight and preferably 50 to 60% moisture content by weight. The percentage moisture by weight may be the weight of water divided by a total weight consisting of the chips of biomass plus a water weight. In the steam explosion stage, the softened and hydrated chips of biomass are exposed to high temperature and high-pressure steam for a sufficient time period, such as 3 minutes to 15 minutes, to create high pressure steam inside the partially hollow cellulose fibers and other porous areas in the bulk structure of the biomass material. (See for example FIG. 4C illustrating a chip of biomass having a fiber bundle of cellulose fibers surrounded and bonded together by lignin but under magnification having numerous porous areas.)

After the thermal hydrating stage, the softened biomass in chip form are any combination of 1) crushed and 2) compressed into a plug form, which is then fed into a continuous screw conveyor system. The continuous screw conveyor system moves the biomass in plug form into the steam explosion stage. The continuous screw conveyor system uses the biomass in plug form to prevent blow back backpressure from the high-pressure steam present in the steam explosion stage from affecting the thermal hydrating stage. Other methods could be used such as 1) check valves and 2) moving biomass in stages where each stage is isolatable by an opening and closing mechanism.

The steam explosion stage can operate at pressures up to 850 psi but stays preferably below 450 psi. A set of sensors may detect the operating pressure. The plug screw feeder conveys the chips along the steam explosion stage. High-pressure steam is introduced into the plug screw feeder in a section called the steam mixing conveyor. The high pressure supply input may consist of several nozzles strategically placed around the steam mixing conveyor. Feed rate of the biomass chip material through the steam explosion stage is accurately controlled via the plug screw feeder. Retention time within the steam explosion stage is controlled separately by the control system. In the steam explosion stage, the biomass in plug form is exposed to high temperature and high pressure steam at at least 160 degree C. and 160 PSI from the high pressure steam input for at least 5 minutes and preferably around 10 minutes until moisture penetrates porous portions of the bulk structure of the biomass and all of the liquids and gases in the biomass are raised to the high pressure. In an embodiment, the steam explosion stage has a set of temperature and pressure sensors and a control system, where the biomass is exposed to high temperature and high pressure steam of at least 188 degrees C. and 160 PSI from the second steam input between 5 minutes to 20 minutes until moisture penetrates porous portions of a bulk structure of the biomass.

As discussed, the Steam Explosion Process works best, when the system has a certain level of humidity/moisture in the biomass chips to provide the source of explosion. So usually, the chip's moisture is generally at least 50 to 55% by weight while in the steam explosion reactor. In the steam explosion stage of the steam explosion unit 108, the pressure and temperature are raised in a chamber containing the chips of biomass with softened lignin to an increased temperature of at least twenty degrees greater than an operating environment of the vessel with chips of biomass in the thermal hydrating stage and to an increased pressure greater than fourteen times atmospheric in the chamber but for a shorter duration than the set period of time in the thermal hydrating stage.

The continuous screw conveyor system feeds the biomass in plug form through the steam explosion stage to a refiner stage. The steam explosion stage couples to a refiner stage that has one or more blades configured to mechanically agitate the pressurized biomass prior to the pressurized biomass exiting the steam explosion stage through the exit orifice to a blow line maintained at a pressure of less than a third of the pressure inside the steam explosion stage in order to internally blow apart the pressurized biomass. The mechanical agitation in the refiner stage is configured to cause resulting biomass in particle form to have a more consistent size distribution of the average dimensions of the biomass particles. The blades of the refiner stage mechanically agitate the pressurized and moistened biomass and send the agitated biomass to the orifice exit.

In an embodiment, a small opening forms the exit and goes into a tube or other container area that is maintained at around 4-10 bar of pressure and any internal fluids or gases at the high pressure expand to internally blow apart the biomass. In some cases, the pressure drop is from the high pressure in the Steam Explosion reactor all the way down to atmospheric pressure. In either case, the large pressure drop occurring in the tube or other container between the exit in the steam explosion stage and a cyclone water removal stage is dropped rapidly. In an embodiment, the pressure drop occurs rapidly by extruding the bulk structure of the biomass at between 160 to 450 PSI into a tube at the dramatically reduced pressure, such as 4-10 bar, to cause an internal "explosion" rapid expansion of steam upon the drop in pressure or due to the "flashing" of liquid water to vapor upon the drop in pressure below its vapor pressure, which internally blows apart the biomass in chip form into minute fine particles of biomass. In another embodiment, the steam explosion reactor portion of the steam explosion stage contains a specialized discharge mechanism configured to "explode" the biomass chip material to a next stage at atmospheric pressure. The discharge mechanism opens to release the biomass from the high-pressure steam explosion reactor out this reactor discharge outlet valve or door into the feed line of the blow tank.

Figure 4D:
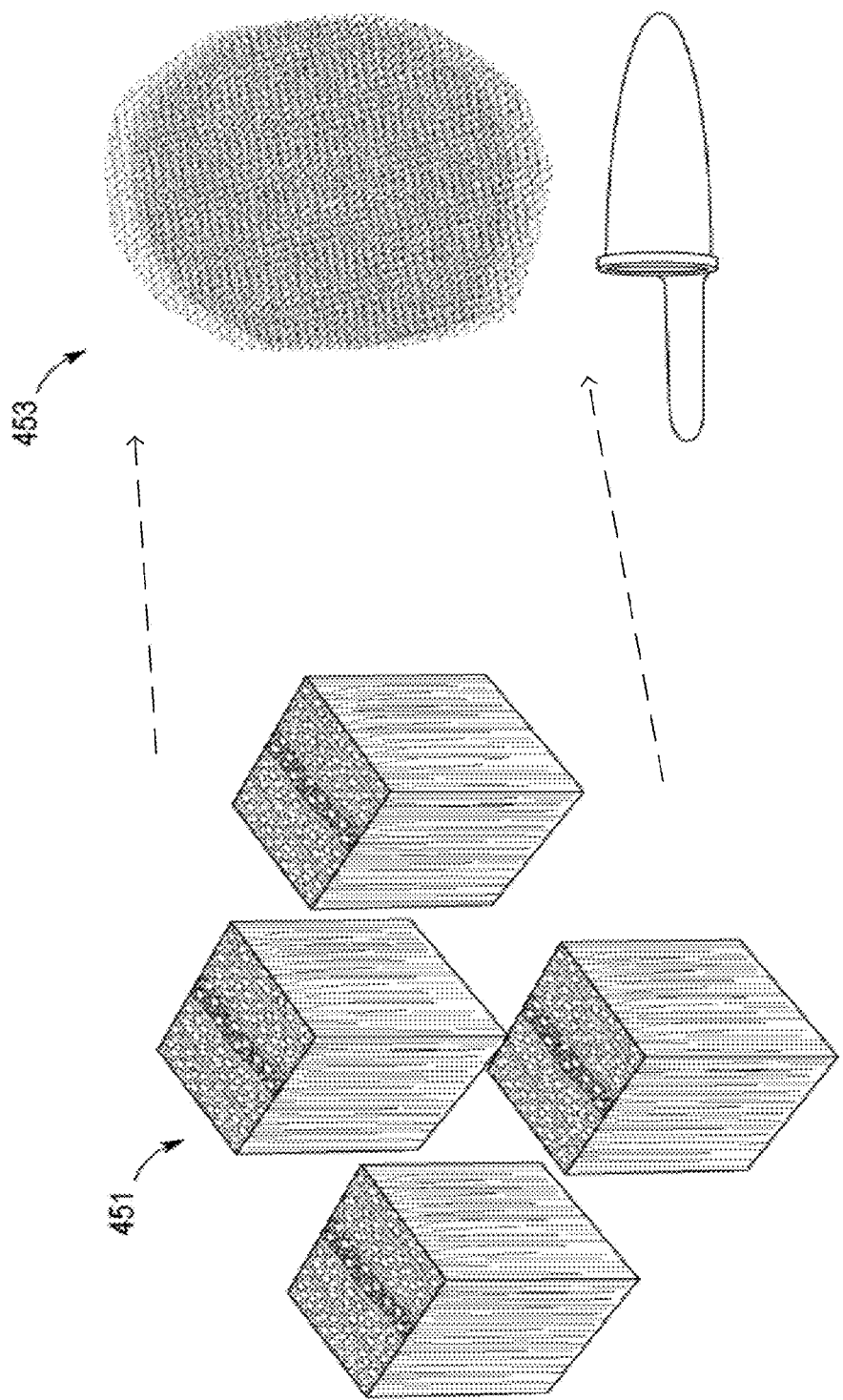
FIG. 4D illustrates example chips of biomass exploded into fine particles of biomass.

Thus, the pressurized steam or super-heated water out of the steam explosion reactor in this stage is then dropped rapidly to cause an explosion, which disintegrates the chips of biomass into minute fine particles. (See for example FIG. 4D illustrating chips of biomass exploded into fine particles of biomass 453.) The original bundle of fibers making up the biomass is exploded into fragments making discrete particles of fine powder. (See for example FIGS. 4A-C illustrating different levels of magnification of a chip of biomass having a fiber bundle of cellulose fibers surrounded and bonded together by lignin and compare to FIG. 4D.)

The moisture and biomass chips are extruded out the reactor discharge to a container, such as the blow line, at approximately atmospheric pressure at the end of the container/blow line. The high-pressure steam or water conversion to vapor inside the partially hollow fibers and other porous areas of the biomass material causes the biomass cell to explode into fine particles of moist powder. The bulk structure of the biomass includes organic polymers of lignin and hemi-cellulose that surrounds a plurality of cellulose fibers. The bulk structure of the biomass is internally blown apart in this SEP step that uses at least moisture, pressure, and heat to liberate and expose the cellulose fibers to be able, as an example, to directly react during the biomass gasification reaction rather than react only after the layers of lignin and hemi-cellulose have first reacted to then expose the cellulose fibers. The high temperatures also lowers the energy/force required to breakdown the biomass' structure as there is a softening of lignin that facilitates fiber separation along the middle lamella.

Thus, internally in the steam explosion stage, a mechanical mechanism opens, such as a valve or door, or merely a small hole exists in the steam explosion reactor. The reactor is filled with softened biomass chips potentially in plug form at high pressure and after a period of time exposes those softened biomass chips to a low pressure that physically blows apart the bulk structure of fiber bundle of the biomass containing the lignin, cellulose fibers, and hemi-cellulose into fragments and separates one from another. When the steam-explosion process operates at lower severities (e.g. 175-185 degrees C. and 160 PSI) in the steam explosion reactor then particles in the size of fragments of small fibers come out of the discharge and at higher severities (e.g. 300 PSI) very, very, fine grains of particles are produced.

The biomass produced into the moist fine particle form from the stages has average dimensions of less than 50 microns thick and less than 500 microns in length. In an embodiment, the steam explosion stage couples to a refiner stage that has one or more blades configured to mechanically agitate the pressurized biomass prior to the pressurized biomass exiting the steam explosion stage through the exit orifice to a blow line and the produced fine particles of biomass with reduced moisture content includes cellulose fibers that are fragmented, torn, shredded and any combination of these and may generally have an average dimension of less than 30 microns thick and less than 250 microns in length. Those produced moist fine particles of biomass are subsequently fed to a feed section of the biomass gasifier 114.

Internally blowing apart the bulk structure of biomass in a fiber bundle into pieces and fragments of cellulose fiber, lignin and hemi-cellulose results in all three 1) an increase of a surface area of the biomass in fine particle form compared to the received biomass in chip form, 2) an elimination of a need to react outer layers of lignin and hemi-cellulose prior to starting a reaction of the cellulose fibers, and 3) a change in viscosity of the biomass in fine particle form to flow like grains of sand rather than like fibers.

The morphological changes to the biomass coming out of SEP reactor can include:

a. No intact fiber structure exists rather all parts are exploded causing more surface area, which leads to higher reaction rates in the biomass gasifier;
b. Fibers appear to buckle, they delaminate, and cell wall is exposed and cracked;
c. Some lignin remains clinging to the cell wall of the cellulose fibers;
d. Hemi-cellulose is partially hydrolyzed and along with lignin are partially solubilized;
e. The bond between lignin and carbohydrates/polysaccharides (i.e. hemi-cellulose and cellulose) is mostly cleaved; and
f. many other changes discussed herein.

The created moist fine particles may be, for example, 20-50 microns thick in diameter and less than 100 microns in length on average. Note, 1 inch=25,400 microns. Thus, the biomass comes from the chipper unit 104 as chips up to 1 inch in length and 0.25 inches in thickness on average and go out as moist fine particles of 20-50 microns thick in diameter and less than 100 microns in length on average, which is a reduction of over 2000 times in size. The violent explosive decompression of the saturated biomass chips occurs at a rate swifter than that at which the saturated high-pressure moisture in the porous areas of the biomass in chip form can escape from the structure of biomass.

Figure 4E:
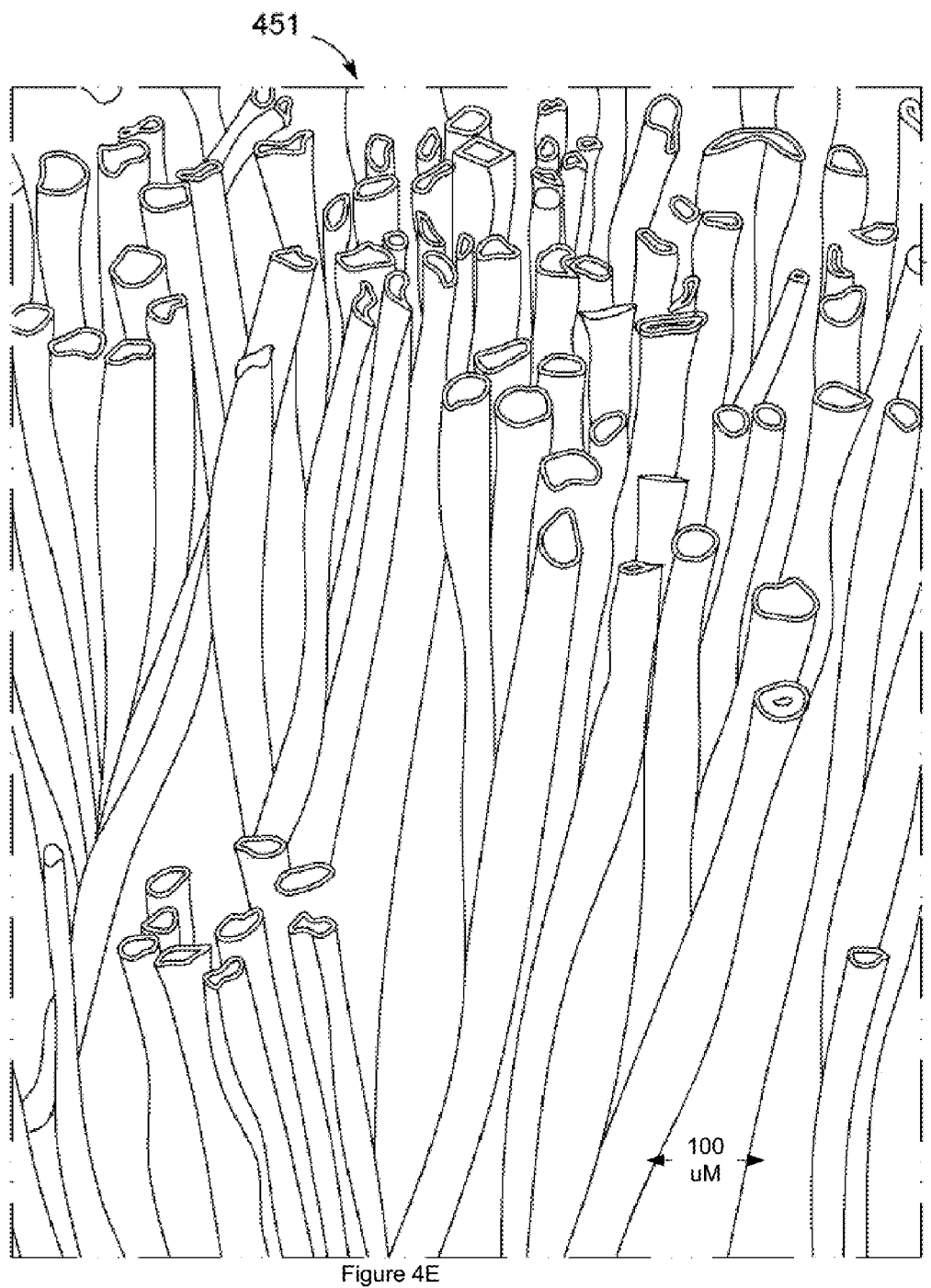
FIG. 4E illustrates a chip of biomass having a bundle of fibers that are frayed or partially separated into individual fibers.

Note, no external mechanical separation of cells or fibers bundle is needed rather the process uses steam to explode cells from inside outward. (See FIG. 4E illustrating a chip of biomass a chip of biomass 451 having a bundle of fibers that are frayed or partially separated into individual fibers.) Use of SEP on the biomass chips produces small fine particles of cellulose and hemi-cellulose with some lignin coating. (See FIG. 4D illustrating example chips of biomass, including a first chip of biomass 451, exploded into fine particles of biomass 453.) This composite of lignin, hemi-cellulose, and cellulose in fine form has a high surface area that can be moved/conveyed in the system in a high density.

The produced fine particles of biomass are fed downstream to the biomass gasifier 114 for the rapid biomass gasification reaction in a reactor of the biomass gasifier 114 because they create a higher surface to volume ratio for the same amount of biomass compared to the received biomass in chip form, which allows a higher heat transfer to the biomass material and a more rapid thermal decomposition and gasification of all the molecules in the biomass.

Please refer to FIG. 1B, for an example where one or more steam supply inputs may include a low pressure steam produced from recycled dirty water recovered from the one or more cyclone units. For example, embodiments as described herein include tapping off-gases from the cyclone unit and feeding the off-gases to the biomass gasifier. Also, those gases and any additional condensate may be fed to a turpentine recovery unit. Thus, gases containing organic compounds coming out of the steam explosion stage that are recovered from the cyclone unit may be collected and fed through a feedline to the biomass gasifier. The biomass gasifier would then convert those gases containing organic compounds into syngas components and other gases.

Turpentine and other volatiles may be delivered to the biomass gasifier via steam atomization of the dirty condensate water recovered from the one or more cyclone units. For example, a feeding steam containing volatiles/turpentine may include off gases from the one or more cyclones and fed into the gasifier. A turpentine recovery unit may be included, with product to sales, the gasifier, or the burner system for the gasifier or reformer. Additionally, dirty water extruded when the biomass is compacted and moved via the screw feed system may be recovered and sent to the Turpentine Recovery Unit.

In an embodiment, cyclic operations are possible rather than a continuous conveyor system. The cyclic operation allows soft moist chips to be loaded into the SEP reactor and then the steam input introduces high temperature and high-pressure steam for 10 minutes to raise the pressure of the gases and liquids in the biomass. After that period, the valve or door opens to extrude biomass particles into feed line into blow tank.

A collection chamber at an outlet stage of the steam explosion stage is used to collect the biomass reduced into smaller particle sizes and in pulp form. One or more cyclone filters can be in line with the feed line to separate water vapor from biomass particles, where biomass particles are then fed into a blow tank.

Note, methods may also be incorporated to reduce pressure in the exit of the steam explosion unit to reduce motive gas. Accordingly, one or more pressure reduction areas may be included to reduce the high pressure from the SEP vessel to a lower discharge pressure. Therefore, the design may include locating pressure drop points out of the steam explosion unit to reduce the pressure from the high pressure in the steam explosion unit to a reduced pressure such as 4-10 bar. The pressure drop may occur earlier in the pipe leading to the cyclone.

Also, in an exemplary embodiment, no additional air is introduced between the SEP pretreatment step of the biomass particles and the entrained gas feeding of the biomass particles into the biomass gasifier, which reduces emissions and purge gases. Options may be included for using the motive gas out of the steam explosion unit for the entrainment gas into the biomass gasifier.

In another embodiment, at an exit of the steam explosion stage, once the biomass in plug form explodes into the moist fine particles form. The steam explosion stage filled with high-pressure steam and/or superheated water contains a discharge outlet configured to "explode" the biomass material to a next stage at atmospheric pressure to produce biomass in fine particle form. The biomass in fine particle form flows through a feed line of a blow tank at high velocity.

The biomass in moist fine particles form enters the feed line of the blow tank. The feed line is initially small, such as only 1.5 in. in diameter, with the particles of the biomass passing through at high velocity. Flow enhancements, such as wax, may be added in initial portion of the blow line while the fibers are still wet to improve material consistency and avoid hydro bonding. The feed line now expands to 60 in. in diameter and the biomass in moist fine particles form has its heat maintained by heating coils traced around and warming the blow line. Maintaining the temperature of the biomass tends to help crystallize the rosins and resin acids of the biomass preventing the fiber particles from conglomerating back together. Thus, the temperature helps to prevent the lignin from clumping and rosins from hardening.

The flow aids, including any of 1) ash recycled from the biomass gasifier 114 and 2) olefins, such as wax, are injected at any of 1) the discharge outlet of the steam explosion stage and 2) in the feed line to prevent clogs by the biomass. In addition, the feed line may have heating coils traced around the feed line to maintain an elevated temperature of the biomass in fine particle form to help prevent crystallization of rosins and resin acids in the biomass in fine particle form.

The produced particles of biomass loses a large percentage of the moisture content due to steam flashing in the blow line and being vented off as a water vapor. The produced particles of biomass and moisture are then separated by a cyclone filter and then fed into a blow tank. Thus, a water separation unit is inline with the blow line. A collection chamber at an outlet stage of the steam explosion stage is used to collect the biomass reduced into smaller particle sizes and in pulp form and is fed to the water separation unit. Water is removed from the biomass in fine particle form in a cyclone unit and/or a dryer unit.

A moisture content of the fine particles of biomass is further dried out at an exit of the blow tank by a dryer unit such as a flash dryer or low temperature torrefaction unit that reduces the moisture content of fine particles of biomass to 1-20% by weight preferably. A goal of the fiber preparation is to create particles of biomass with maximum surface area and as dry as feasible to 5-20% moisture by weight of the outputted biomass fine particle. The flash dryer merely blows hot air to dry the biomass particles coming out from the blow tank. The flash dryer can be generally located at the outlet of the blow tank or replace the cyclone at its entrance to make the outputted biomass particles contain a greater than 5% but less than 20% moisture content by weight. The flash dryer may feed the biomass to a silo for storage to further dry out the SEP fine particles of biomass prior to being fed into a lock hopper. In an embodiment, a paddle dryer can reduce the biomass particle size further due to the velocity of the gas carrying the particles going into the dryer it acts as a mill on the incoming particles of biomass.

The resulting particles of biomass differs from Thermal Mechanical Pulping (TMP) in that particles act more like crystal structures and flows easier than fibers which tend to entangle and clump.

The reduced moisture content of 5% to about 35% by weight of the biomass in fine particle form is fed by a conveying system, as an example, to a torrefaction unit 112 to undergo torrefaction or pyrolysis at a temperature from 100 to 700 degrees C. for a preset amount of time.

A conveyor system supplies the biomass in particle form to a torrefaction unit 112 to process the biomass at a temperature of less than 700 degrees C. for a preset amount of time to create off gases to be used in a creation of a portion of the syngas components that are collected by a tank and may be eventually fed to an organic liquid product synthesis reactor such as the methanol synthesis reactor.

The fine particles of biomass out of the blow tank and flash dryer has a low moisture content already due to the steam flashing, further air drying, and are a composite of fragments of cellulose fibers with a lignin coating, pieces of lignin, cellulose, and hemi-cellulose, etc. The biomass gasifier 114 has a reactor vessel configured to react the biomass in moist fine particle form with an increased surface area due to being blown apart by the steam explosion unit 108. The biomass gasifier 114 has a high pressure steam supply input and one or more heaters, and in the presence of the steam the biomass in fine particle form are reacted in the reactor vessel in a rapid biomass gasification reaction between 0.1 and 5.0 second resident time to produce at least syngas components, including hydrogen (H2) and carbon monoxide (CO). When the fine particles produced are supplied in high density to the biomass gasifier 114, then the small particles react rapidly and decompose the larger hydrocarbon molecules of biomass into the syngas components more readily and completely. Thus, nearly all of the biomass material lignin, cellulose fiber, and hemi-cellulose completely gasify rather than some of the inner portions of the chip not decomposing to the same extent to that the crusted shell of a char chip decomposes. These fine particles compared to chips create less residual tar, less carbon coating and less precipitates. Thus, breaking up the integrated structure of the biomass in a fiber bundle tends to decrease an amount of tar produced later in the biomass gasification. These fine particles also allow a greater packing density of material to be fed into the biomass gasifier 114. As a side note, having water as a liquid or vapor present at at least 10 percent by weight may assist in generating methanol CH3OH as a reaction product in addition to the CO and H2 produced in the biomass gasifier 114.

The torrefaction unit and biomass gasifier 114 may be combined as an integral unit.

In the alternative, the moist blown apart particles of biomass may be fed in slurry form from the output of the steam explosion reactor directly, or after drying, to a pelletizer. The pelletizer may densify the biomass from fine particle form into pellets of biomass, which those pellets are then fed into the biomass gasifier. This direct feed and conversion of biomass from fine particle form to pellet form saves multiple steps and lots of energy consumption involved in those eliminated steps. Alternatively, the pellets may be transported to facilities for further processing to liquid fuel, heat/power, animal feed, litter, or chemicals.

In an embodiment, the biomass gasifier 114 is designed to radiantly transfer heat to particles of biomass flowing through the reactor design with a rapid gasification residence time, of the biomass particles of 0.1 to 10 seconds and preferably less one second. The biomass particles and reactant gas flowing through the radiant heat reactor primarily are driven from radiant heat from the surfaces of the radiant heat reactor and potentially heat transfer aid particles entrained in the flow. The reactor may heat the particles in a temperature in excess of generally 900 degrees C. and preferably at least 1200° C. to produce the syngas components including carbon monoxide and hydrogen, as well as keep produced methane at a level of ≤1% of the compositional makeup of exit products, minimal tars remaining in the exit products, and resulting ash.

Figure 2:
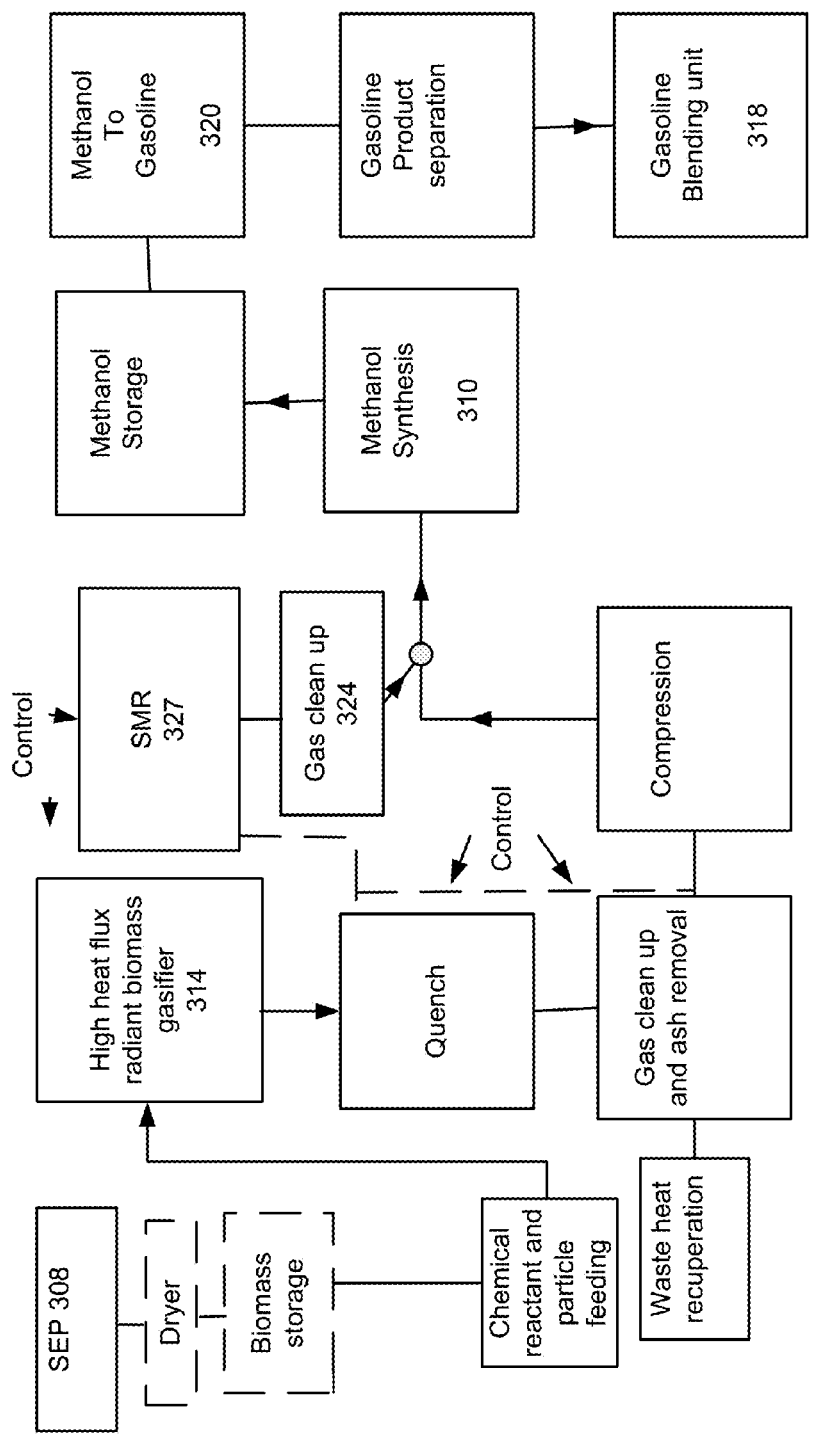
FIG. 2 illustrates an embodiment of a flow diagram of an integrated plant to generate syngas from biomass and generate a liquid fuel product from the syngas.
Figures 1, 3:
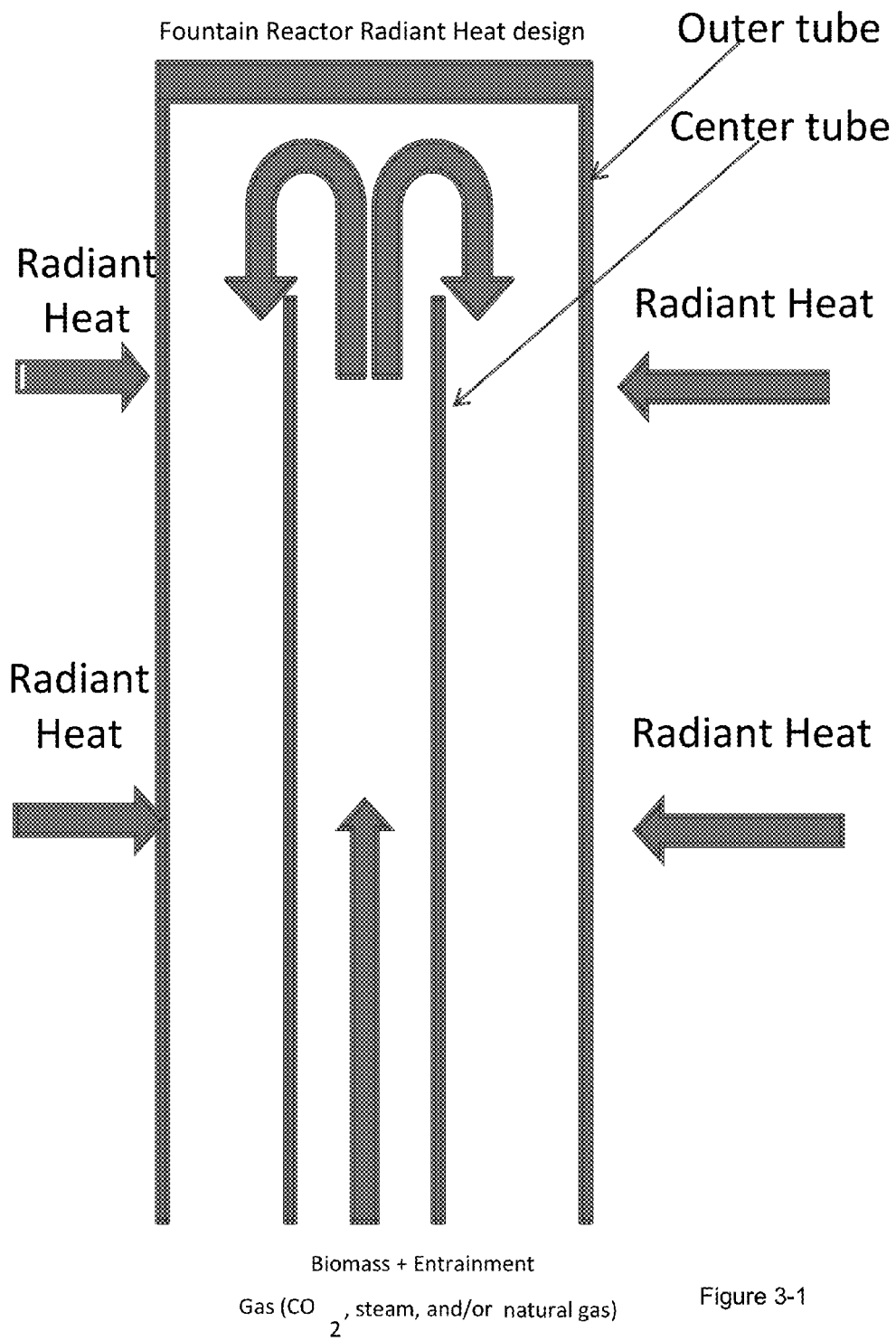
FIGS. 3-1 to 3-4 illustrate alternative configurations for exemplary biomass gasifiers.
Figures 2, 3:
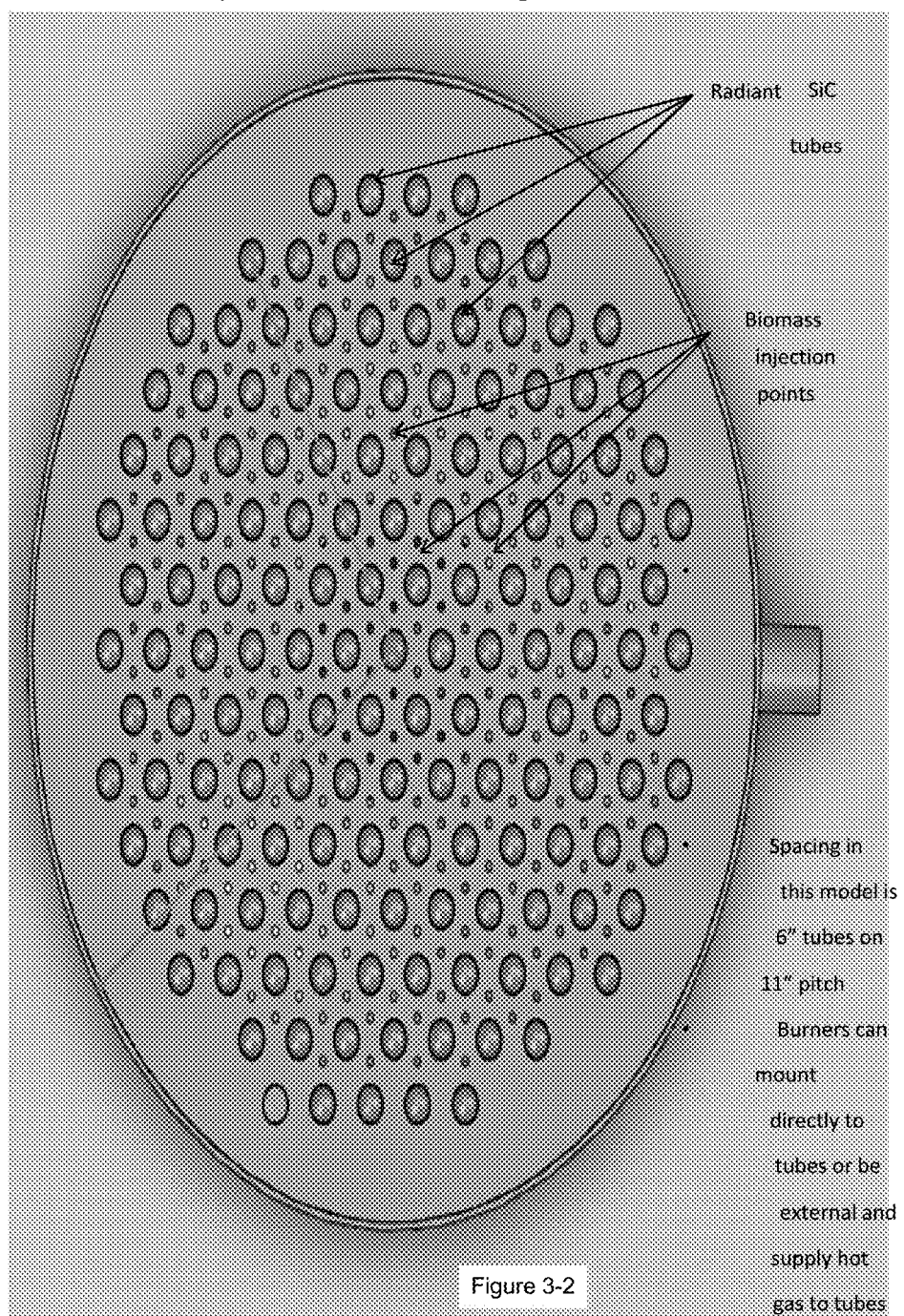
Figures 3, 4:
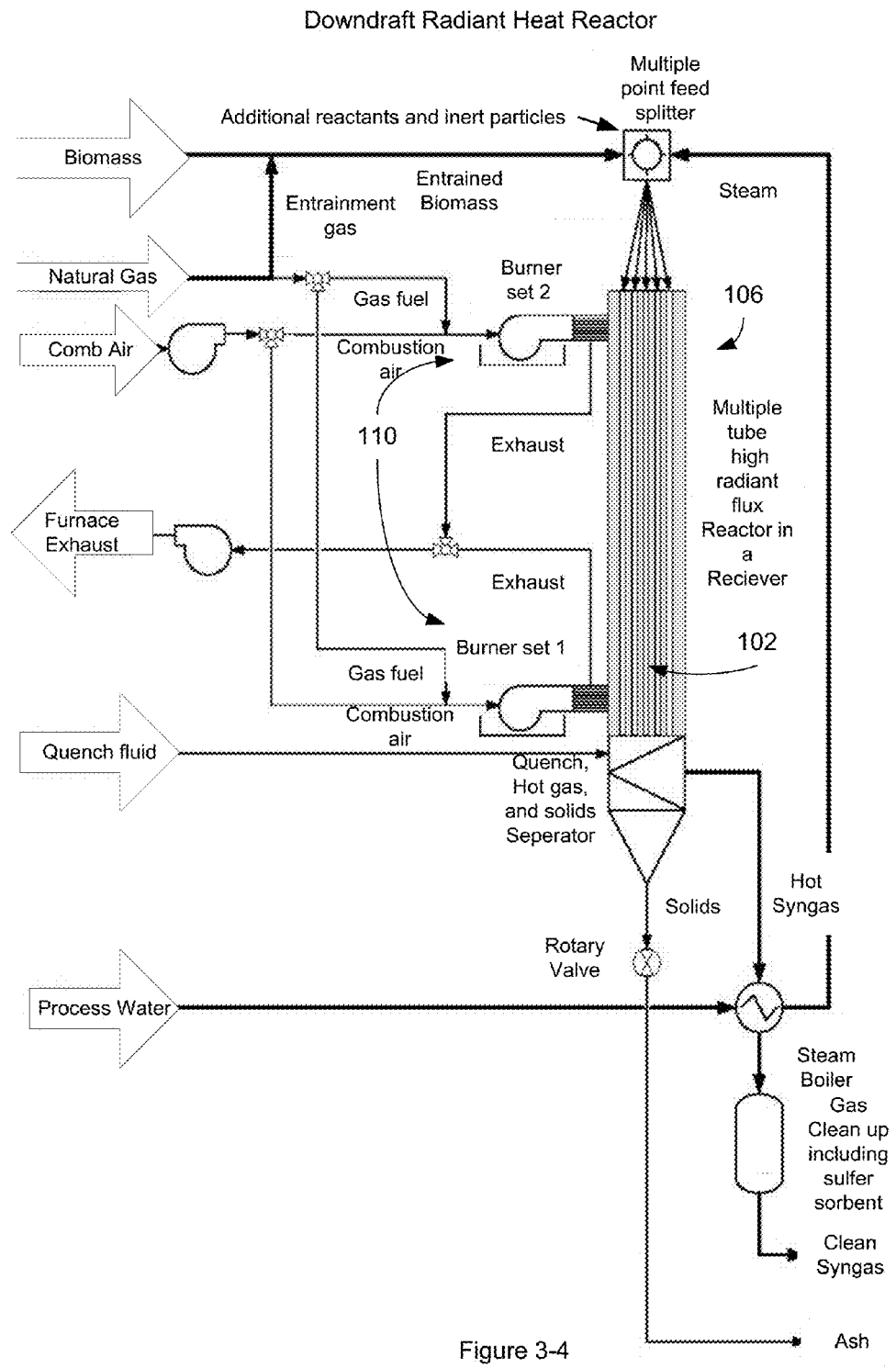

FIGS. 3-1 to 3-4 illustrate exemplary embodiments of the biomass gasifier 114. FIG. 3-1 illustrates a fountain reactor using radiant heat in which entrainment gases carrying biomass enter at the bottom of the gasifier and are projected through a center tube and fountain over a separation wall created by the center tube and fall in a section created between an outer tube and the center tube. FIGS. 3-2 and 3-3 illustrate an exemplary bayonet reactor radiant heat design where a series of radiant heat tubes are used to heat injected biomass. Gas fired burners can provide heat directly to the tubes or to an intermediate source, such as a heating gas, supplied to the tubes. The biomass may be external to the tubes, while heat is supplied internal to the tubes. Alternatively, the biomass may be in between the tube sheet and the refractory lining. FIG. 3-4 illustrates an exemplary downdraft radiant heat reactor in which multiple tubes are used to provide radiant heat to the reactor. The biomass may either be external to the tubes, while heat is supplied internal to the tubes, or visa-versa.

The thermal receiver 106 has a cavity with an inner wall. The radiation driven geometry of the cavity wall of the thermal receiver 106 relative to the reactor tubes 102 locates the multiple tubes 102 of the chemical reactor as offset and in a staggered arrangement inside the receiver 106. A surface area of the cavity walls is greater than an area occupied by the reactor tubes 102 to allow radiation to reach areas on the tubes 102 from multiple angles. The inner wall of the receiver 106 cavity and the reactor tubes 102 exchange energy primarily by radiation, with the walls and tubes 102 acting as re-emitters of radiation to achieve a high radiative heat flux reaching all of the tubes 102, and thus, avoid shielding and blocking the radiation from reaching the tubes 102, allowing for the reactor tubes 102 to achieve a fairly uniform temperature profile from the start to the end of the reaction zone in the reactor tubes 102.

Thus, the geometry of the reactor tubes 102 and cavity wall shapes a distribution of incident radiation with these 1) staggered and offset tubes 102 that are combined with 2) a large diameter cavity wall compared to an area occupied by the enclosed tubes 102, and additionally 3) combined with an inter-tube radiation exchange between the multiple reactor tube geometric arrangement relative to each other where the geometry. The wall is made of material that highly reflects radiation or absorbs and re-emits the radiation. The shaping of the distribution of the incident radiation uses both reflection and absorption of radiation within the cavity of the receiver 106. Accordingly, the inner wall of the thermal receiver 106 is aligned to and acts as a radiation distributor by either 1) absorbing and re-emitting radiant energy, 2) highly reflecting the incident radiation to the tubes 102, or 3) any combination of these, to maintain an operational temperature of the enclosed ultra-high heat flux chemical reactor. The radiation from the 1) cavity walls, 2) directly from the regenerative burners, and 3) from an outside wall of other tubes acting as re-emitters of radiation is absorbed by the reactor tubes 102, and then the heat is transferred by conduction to the inner wall of the reactor tubes 102 where the heat radiates to the reacting particles and gases at temperatures between 900 degrees C. and 1600 degrees C., and preferably above 1100 degrees C.

As discussed, the inner wall of the cavity of the receiver 106 and the reactor tubes 102 exchange energy between each other primarily by radiation, not by convection or conduction, allowing for the reactor tubes 102 to achieve a fairly uniform temperature profile even though generally lower temperature biomass particles and entrainment gas enter the reactor tubes 102 in the reaction zone from a first entrance point and traverse through the heated cavity to exit the reaction zone at a second exit point. This radiation heat transfer from the inner wall and the reactor tubes 102 drives the chemical reaction and causes the temperature of the chemical reactants to rapidly rise to close to the temperature of the products and other effluent materials departing from the exit of the reactor.

A length and diameter dimensions of a gasification reaction zone of each of the reactor tubes 102 is sized to give the residence time of greater than 0.1 second at the gasification temperatures of at least 900 degrees C., and an exit of the gasification zone in the multiple reactor tubes 102. The reaction products have a temperature from the exit of the gasification zone that equals or exceeds 900 degrees C., and the multiple reactor tubes 102 in this chemical reactor design increase available reactor surface area for radiative exchange to the biomass particles, as well as inter-tube radiation exchange. A rapid gasification of dispersed falling biomass particulates with a resultant stable ash formation occurs within a residence time within the reaction zone in the reactor tubes 102, resulting in a complete amelioration of tar to less than 500 milligrams per normal cubic meter, and at least a 90% conversion of the biomass into the production of the hydrogen and carbon monoxide products.

To achieve high conversion and selectivity, biomass gasification requires temperatures in excess of 1000° C. These are difficult to achieve in standard fluidized bed gasifiers, because higher temperatures requires combustion of an ever larger portion of the biomass itself. As a result, indirect and fluidized bed gasification is typically limited to temperatures of 800° C. At these temperatures, production of unwanted higher hydrocarbons (tars) is significant. These tars clog up downstream equipment and foul/deactivate catalyst surfaces, requiring significant capital investment (10-30% of total plant cost) in tar removal equipment. High heat flux thermal systems are able to achieve high temperatures very efficiently. More importantly, the efficiency of the process can be controlled as a function of concentration and desired temperature, and is no longer linked to the fraction of biomass lost to achieving high temperature. As a result, temperatures in the tar cracking regime (1000-1300° C.) can be achieved without any loss of fuel yield from the biomass or overall process efficiency. This removes the complex train of tar cracking equipment typically associated with a biomass gasification system. Additionally, operation at high temperatures improves heat transfer and decreases required residence time, decreasing the size of the chemical reactor and its capital cost.

The temperatures of operation, clearly delineated with wall temperatures between 1200° C. and 1450° C. and exit gas temperatures in excess of 900° C. but not above silica melting temperatures (1600° C.) is not typically seen in gasification, and certainly not seen in indirect (circulating fluidized bed) gasification. The potential to do co-gasification of biomass and steam reforming of natural gas, which can be done in the ultra-high heat flux chemical reactor, could not be done in a partial oxidation gasifier (as the methane would preferentially burn). The process' feedstock flexibility derives from the simple tubular design, and most gasifiers, for reasons discussed herein, cannot handle a diverse range of fuels.

A material making up the inner wall of the receiver 306 cavity may have mechanical and chemical properties to retain its structural strength at high temperatures between 1100-1600° C., have very high emissivity of $\epsilon > 0.8$ or high reflectivity of $\epsilon < 0.2$, as well as high heat capacity (>200 J/kg-K), and low thermal conductivity (<1 W/m-K) for the receiver 306 cavity. A material making up the reactor tubes 302 possesses high emissivity ($\epsilon > 0.8$), high thermal conductivity (>1 W/m-K), moderate to high heat capacity (>150 J/kg-K).

An example Particle Size Analysis to determine the particle size can be a Digital Image Processing Particle Size and Shape Analysis System such as a Horiba, Ltd. Camsizer XT particle size analyzer. Such a system uses one or more cameras to provide rapid and precise particle size and particle shape distributions for dry powders and bulk material in the size range, for example, from 30 µm to 30 mm. The measurements from the digital image processing system allows a correlation to existing data from techniques as diverse as sieving and sedimentation, which in some instances may also be used to measure particle size. In an embodiment, the particle size of the steam exploded wood chips are measured using a Horiba, Ltd. Camsizer XT particle size analyzer. The sample to be measured is mixed in a resealable bag by kneading and agitating the material in the bag by external manipulation. After mixing, a sample amount, such as approximately 3 cm^3, is loaded into the sample hopper of the instrument. The target is to run and analyze enough sample size, such as at least 2 million particles from each sample, so the sample volume is only important insofar as it corresponds to an adequate number of particles. Example settings on the instrument can be as follows 0.2% covered area, image rate 1:1, with X-Jet, gap width=4.0 mm, dispersion pressure=380.0 kPa, xFe_max [and xc_min, accordingly]. Feed rate is controlled to yield a target covered area so that the computer can process the images quickly enough. The camera imaging rate is fixed, and both "basic" and zoom images are obtained for every run. A single value for average particle size, such as the diameter is less than 50 microns, may be the objective measurement standard. In an embodiment, a three point value for both Fe-max and xc-min is more complete. So that's like a 6 point value. The particle size distribution (PSD) may be defined as Fe-Max D10, D50, D90 and Xc-min D10, D50, D90. The measurement then can use multiple values such as input 6 values to determine the measurement. Other similar mechanisms may be used.

Calculations can be made using Fe max and xc min on a volume basis. Two models can be used to analyze the particle images: xc-min, which yields results comparable to those obtained by physically screening/sieving samples, and Fe-max, which is similar to measuring the longest dimension of a given particle with a caliper. Raw data, frequency plots, binned results, and particle images are obtained for all samples. D10, D50, and D90 may be calculated on a volume basis, as is the average aspect ratio. D90 describes the diameter where ninety percent of the distribution has a smaller particle size and ten percent has a larger particle size. The D10 diameter has ten percent smaller and ninety percent larger. A three point specification featuring the D10, D50, and D90 is considered complete and appropriate for most particulate materials. In an embodiment, the particle size distribution PSD may be defined as D50 (µm) Model Fe-max.

TABLE 1

Particle size distributions for steam exploded wood
Particle size indices for SEP-processed samples generated from xc-min and Fe-max models.

| Example | Model | D10 (µm) | D50 (µm) | D90 (µm) | Avg. Aspect |
|---|---|---|---|---|---|
| SEP White Pine #1 | xc-min | 20.4 | 59.8 | 176 | 0.47 |
| SEP White Pine #2 | xc-min | 23.9 | 71.7 | 213 | 0.48 |
| SEP White Pine #2-a | xc-min | 21.7 | 65.3 | 197 | 0.49 |
| SEP White Pine #3 | xc-min | 23 | 59.5 | 182 | 0.47 |
| SEP Mixed Hardwood #4 | xc-min | 39.3 | 175.0 | 404.1 | — |
| SEP Black Spruce #5 | xc-min | 25.6 | 94.4 | 320 | 0.45 |
| SEP White Pine #1 | Fe-max | 34.5 | 158 | 541 | 0.47 |
| SEP White Pine #2 | Fe-max | 41.4 | 186 | 660 | 0.45 |

TABLE 1-continued

Particle size distributions for steam exploded wood
Particle size indices for SEP-processed samples generated
from xc-min and Fe-max models.

| Example | Model | D10 (µm) | D50 (µm) | D90 (µm) | Avg. Aspect |
|---|---|---|---|---|---|
| SEP White Pine #2-a | Fe-max | 39.2 | 176 | 584 | 0.46 |
| SEP White Pine #3 | Fe-max | 42.9 | 186 | 629 | 0.45 |
| SEP Mixed Hardwood #4 | Fe-max | 37 | 168 | 397 | — |
| SEP Black Spruce #5 | Fe-max | 44.7 | 238 | 878 | 0.44 |

The examples in Table 1 were produced with a Steam Pressure of 16 bar and a reaction time of 10 minutes.

FIG. 2 illustrates an embodiment of a flow diagram of an integrated plant to generate syngas from biomass and generate a liquid fuel product from the syngas. The steam explosion unit 308 may have a steam explosion stage and a thermal hydrating stage that supplies particles of biomass either to a dryer, a torrefaction unit, or directly to the biomass gasifier 314. The dryer may be a flash dryer, a drum dryer, a paddle dryer, air dryer, or similar such device.

In an embodiment, a conveying system coupled to a collection chamber at the outlet stage of the steam explosion unit 308 and cyclones supplies biomass in particle form either to a torrefaction unit 312, or directly to the biomass gasifier 314, or to a flash dryer. A majority of the initial lignin and cellulose making up the biomass in the receiver section of the steam tube stage in the steam explosion unit 308 remains in the produced particles of biomass but now is substantially separated from the cellulose fibers in the collection chamber at the outlet stage of the steam explosion stage 308.

The collection chamber in the steam explosion unit 308 is configured to collect non-condensable hydrocarbons from any off gases produced from the biomass during the steam explosion process.

After the steam explosion stage 308, water is removed from the biomass in a water separation unit, for example, a cyclone unit, and the reduced moisture content biomass made of loose fibers and separated lignin and cellulose may be fed to a dryer.

In an embodiment, one or more gas collection tanks in the steam explosion unit 308 may collect non-condensable hydrocarbons from any off gases produced from the biomass during the SEP process and send those non-condensable hydrocarbons with any collected in the torrefaction unit 312 to a catalytic converter 316.

In another embodiment, the reduced moisture content pulp may go directly from the steam explosion unit 308 to the biomass gasifier 314, a torrefaction unit 312, or to a catalytic converter 316. Generally, the particles of biomass go to the torrefaction unit 312 and then onto the biomass gasifier 314. However, the torrefaction unit 312 and biomass gasifier may be combined into a single unit.

The general compositions of biomass types that can be blended, for example, include:

| Component | Wood | Non-wood |
|---|---|---|
| Cellulose | 40-45% | 30-45% |
| Hemi cellulose | 23-35% | 20-35% |
| Lignin | 20-30% | 10-25% |

The biomass gasifier 314 has a reactor configured to react particles of the biomass broken down by the two or more stages of the steam explosion unit 308 and those biomass particles are subsequently fed to a feed section of the biomass gasifier 314. The biomass gasifier 314 has a high temperature steam supply input and one or more heaters and in the presence of the steam the particles of the biomass broken down by the steam explosion unit 308 are reacted in the reactor vessel in a rapid biomass gasification reaction at a temperature of greater than 700 degrees C. in less than a five second residence time in the biomass gasifier 314 to create syngas components, including hydrogen (H2) and carbon monoxide (CO), which are fed to a methanol (CH3OH) synthesis reactor 310. In the gasifier 314, the heat transferred to the biomass particles made up of loose or fragments of cellulose fibers, lignin, and hemicellulose no longer needs to penetrate the layers of lignin and hemicellulose to reach the fibers. In some embodiments, the rapid biomass gasification reaction occurs at a temperature of greater than 700 degrees C. to ensure the minimization of tars from forming during the gasification reaction. Thus, a starting temperature of 700 degrees but less than 950 degrees is potentially a significant range of operation for the biomass gasifier. All of the biomass gasifies more thoroughly and readily.

The biomass gasifier 314 may have a radiant heat transfer to particles flowing through the reactor design with a rapid gasification residence time, of the biomass particles of 0.1 to 10 seconds and preferably less one second, of biomass particles and reactant gas flowing through the radiant heat reactor, and primarily radiant heat from the surfaces of the radiant heat reactor and particles entrained in the flow heat the particles and resulting gases to a temperature in excess of generally 700 degrees C. and preferably at least 1200° C. to produce the syngas components including carbon monoxide and hydrogen, as well as keep produced methane at a level of ≤1% of the compositional makeup of exit products, minimal tars remaining in the exit products, and resulting ash. In some embodiments, the temperature range for biomass gasification is greater than 800 degrees C. to 1400 degrees C.

Referring to FIG. 2, the plant uses any combination of the three ways to generate syngas for methanol production. Syngas may be a mixture of carbon monoxide and hydrogen that can be converted into a large number of organic compounds that are useful as chemical feed stocks, fuels, and solvents. For example, the biomass gasifier 314 gasifies biomass at high enough temperatures to eliminate a need for a catalyst to generate hydrogen and carbon monoxide for methanol production.

Biomass gasification is used to decompose the complex hydrocarbons of biomass into simpler gaseous molecules, primarily hydrogen, carbon monoxide, and carbon dioxide. Some mineral ash and tars are also formed, along with methane, ethane, water, and other constituents. The mixture of raw product gases vary according to the types of biomass feedstock used and gasification processes used.

The biomass gasifier is followed by a gas clean up section to clean ash, sulfur, water, and other contaminants from the syngas gas stream exiting the biomass gasifier 314. The syngas is then compressed to the proper pressure needed for methanol synthesis. Additional syngas from steam methane reformer 327 may connect upstream or downstream of the compression stage.

The synthesis gases of H2 and CO from the gasifier and the steam methane reformer 327 are sent to the common input to the one or more methanol synthesis reactors. The exact ratio of Hydrogen to Carbon monoxide can be optimized by a control system receiving analysis from monitoring equipment on the compositions of syngas exiting the biomass gasifier 314 and steam methane reformer 327 and causing the optimize the ratio for methanol synthesis. The methanol produced by the one or more methanol synthesis reactors is then processed in a methanol to gasoline process.

The liquid fuel produced in the integrated plant may be gasoline or another such as diesel, jet fuel, or some alcohols.

Thus, both the biomass gasifier 314 and the SMR 327 can supply syngas components to the downstream organic liquid product synthesis reactor, such as methanol synthesis reactor 310. The methanol is then supplied to a methanol to gasoline process to create a high quality and high octane gasoline. The methanol may also be supplied to other liquefied fuel processes including jet fuel, DME, gasoline, diesel, and mixed alcohol.

FIGS. 4A-C illustrates different levels of magnification of an example chip of biomass 451 having a fiber bundle of cellulose fibers surrounded and bonded together by lignin.

FIG. 4D illustrates example chips of biomass, including a first chip of biomass 451, exploded into fine particles of biomass 453.

FIG. 4E illustrates a chip of biomass 451 having a bundle of fibers that are frayed or partially separated into individual fibers.

Figure 5:
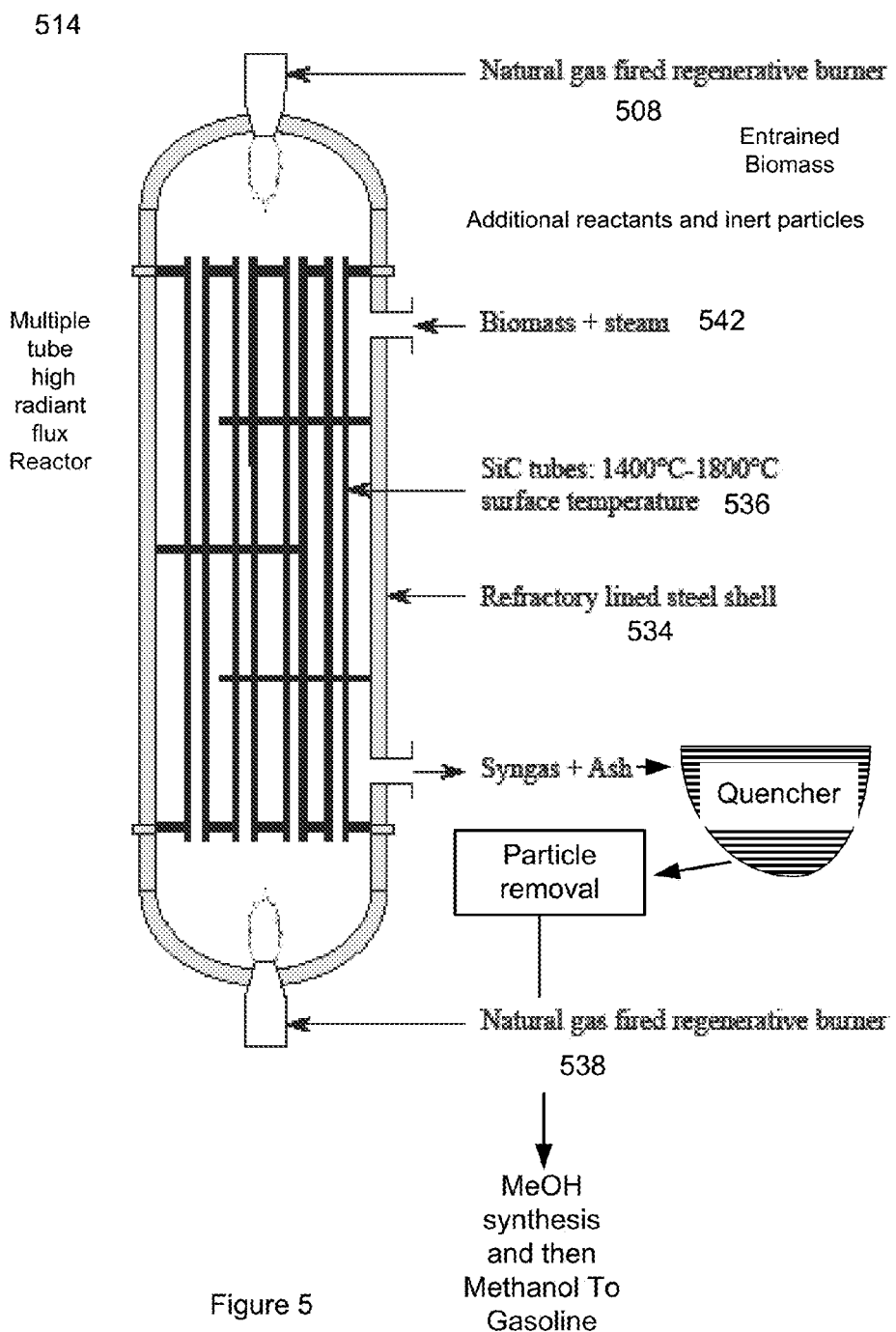
FIG. 5 illustrates a flow schematic of an embodiment for the radiant heat chemical reactor configured to generate chemical products including synthesis gas products.

FIG. 5 illustrates a flow schematic of an embodiment for the radiant heat chemical reactor configured to generate chemical products including synthesis gas products. The multiple shell radiant heat chemical reactor 514 includes a refractory vessel 534 having an annulus shaped cavity with an inner wall. The radiant heat chemical reactor 514 has two or more radiant tubes 536 made out of a solid material. The one or more radiant tubes 536 are located inside the cavity of the refractory lined vessel 534.

The exothermic heat source 538 heats a space inside the tubes 536. Thus, each radiant tube 536 is heated from the inside with an exothermic heat source 538, such as regenerative burners or gas fired burners, at each end of the tube 536. Each radiant tube 536 is heated from the inside with fire and gases from the burners through heat insertion inlets at each end of the tube 536 and potentially by one or more heat insertion ports located in between the two ends. Flames and heated gas of one or more natural gas fired burners 538 act as the exothermic heat source supplied to the multiple radiant tubes at temperatures between 900° C. and 1800° C. and connect to both ends of the radiant tubes 536. Each tube 536 may be made of SiC or other similar material.

One or more feed lines 542 supply biomass and reactant gas into the top or upper portion of the chemical reactor 514. The feed lines 542 for the biomass particles and steam enter below the entry points in the refractory lined vessel 534 for the radiant tubes 536 that are internally heated. The feed lines 112 are configured to supply chemical reactants including 1) biomass particles, 2) reactant gas, 3) steam, 4) heat transfer aid particles, or 5) any of the four into the radiant heat chemical reactor. A chemical reaction driven by radiant heat occurs outside the multiple radiant tubes 536 with internal fires. The chemical reaction driven by radiant heat occurs within an inner wall of a cavity of the refractory lined vessel 534 and an outer wall of each of the one or more radiant tubes 536.

The chemical reaction may be an endothermic reaction including one or more of 1) biomass gasification ($CnHm+H2O \rightarrow CO+H2+H2O+X$), 2) and other similar hydrocarbon decomposition reactions, which are conducted in the radiant heat chemical reactor 514 using the radiant heat. A steam ($H2O$) to carbon molar ratio is in the range of 1:1 to 1:4, and the temperature is high enough that the chemical reaction occurs without the presence of a catalyst.

The biomass particles used as a feed stock into the radiant heat reactor design conveys the beneficial effects of increasing and being able to sustain process gas temperatures of excess of 1200 degrees C. through more effective heat transfer of radiation to the particles entrained with the gas, increased gasifier yield of generation of syngas components of carbon monoxide and hydrogen for a given amount of biomass fed in, and improved process hygiene via decreased production of tars and C2+ olefins. The control system for the radiant heat reactor matches the radiant heat transferred from the surfaces of the reactor to a flow rate of the biomass particles to produce the above benefits.

The control system controls the gas-fired burners 538 to supply heat energy to the chemical reactor 514 to aid in causing the radiant heat driven chemical reactor to have a high heat flux. The inside surfaces of the chemical reactor 514 are aligned to 1) absorb and re-emit radiant energy, 2) highly reflect radiant energy, and 3) any combination of these, to maintain an operational temperature of the enclosed ultra-high heat flux chemical reactor 514. Thus, the inner wall of the cavity of the refractory vessel and the outer wall of each of the one or more tubes 536 emits radiant heat energy to, for example, the biomass particles and any other heat-transfer-aid particles present falling between an outside wall of a given tube 536 and an inner wall of the refractory vessel. The refractory vessel thus absorbs or reflects, via the tubes 536, the concentrated energy from the burners 538 positioned along on the top and bottom of the refractory vessel to cause energy transport by thermal radiation and reflection to generally convey that heat flux to the biomass particles, heat transfer aid particles and reactant gas inside the chemical reactor. The inner wall of the cavity of the thermal refractory vessel and the multiple tubes 536 act as radiation distributors by either absorbing radiation and re-radiating it to the heat-transfer-aid particles or reflecting the incident radiation to the heat-transfer-aid particles. The radiant heat chemical reactor 514 uses an ultra-high heat flux and high temperature that is driven primarily by radiative heat transfer, and not convection or conduction.

Convection biomass gasifiers used generally on coal particles typically at most reach heat fluxes of 5-10 kW/m^2. The high radiant heat flux biomass gasifier will use heat fluxes significantly greater, at least three times the amount, than those found in convection driven biomass gasifiers (i.e. greater than 25 kW/m^2). Generally, using radiation at high temperature (>950 degrees C. wall temperature), much higher fluxes (high heat fluxes greater than 80 kW/m^2) can be achieved with the properly designed reactor. In some instances, the high heat fluxes can be 100 kW/m^2-250 kW/m^2.

Next, the various algorithms and processes for the control system may be described in the general context of computer-executable instructions, such as program modules, being executed by a computer. Generally, program modules include routines, programs, objects, components, data structures, etc. that perform particular tasks or implement particular abstract data types. Those skilled in the art can implement the description and/or figures herein as computer-executable instructions, which can be embodied on any form of computer readable media discussed below. In general, the program modules may be implemented as software instructions, Logic blocks of electronic hardware, and a combination of both. The software portion may be stored on a machine-readable medium and written in any number of programming languages such as Java, C++, C, etc. The machine-readable medium may be a hard drive, external drive, DRAM, Tape Drives, memory sticks, etc. but do not encompass transitory signals. Therefore, the algorithms and controls systems may be fabricated exclusively of hardware logic, hardware logic interacting with software, or solely software.

While some specific embodiments of the design have been shown the design is not to be limited to these embodiments. For example, the recuperated waste heat from various plant processes can be used to pre-heat combustion air, or can be used for other similar heating means. Regenerative gas burners or conventional burners can be used as a heat source for the furnace. The Steam Methane Reforming may be/include a SHR (steam hydrocarbon reformer) that cracks short-chained hydrocarbons (<C20) including hydrocarbons (alkanes, alkenes, alkynes, aromatics, furans, phenols, carboxylic acids, ketones, aldehydes, ethers, etc., as well as oxygenates into syngas components. The design is to be understood as not limited by the specific embodiments described herein, but only by scope of the appended claims.

The invention claimed is:

1. An integrated plant to generate syngas from biomass, comprising:
a steam explosion unit having an input cavity to receive chips of biomass as a feedstock;
three or more steam supply inputs including a first steam supply input, a second steam supply input, and a third steam supply input;
a biomass gasifier having one or more heat sources and a reactor vessel configured to react the biomass in moist fine particle form, wherein the biomass gasifier is connected to at least the third steam supply input;
two or more stages to pre-treat the biomass having an exit orifice connected to to the biomass gasifier, wherein the two or more stages are connected to at least the first and second steam supply units; and
a controller programmed to apply steam from the first steam supply input to degrade bonds between lignin and hemi-cellulose from cellulose fibers of the biomass and increase a moisture content of the received chips of biomass in the two or more stages, apply steam from the second steam supply input at least fourteen times atmospheric pressure to heat and pressurize any gases and fluids present inside the biomass in the two or more stages, and blow apart the biomass via rapid depressurization at the exit orifice to produce particles of the fine particle form exiting from the two or more stages having average dimensions of less than 70 microns thick and less than 500 microns in length,
where the biomass gasifier is configured to produce syngas from the fine particle form and steam, and
where the steam explosion unit and the biomass gasifier are part of the integrated plant.

2. The integrated plant of claim 1,
where the two or more stages of the steam explosion unit and include at least a thermal hydrating stage and a steam explosion stage,
where the thermal hydrating stage has the input cavity to receive the chips of biomass and the first steam supply input is configured to apply low pressure saturated steam into a vessel containing the chips of biomass at an elevated temperature of above 60 degrees C. but less than 145 degrees C. and at a pressure around atmospheric pressure, to start a decomposition, hydrating, and softening of the received chips of biomass,
where a set of temperature sensors provides feedback on the elevated temperature of the received chips of biomass, and
where a first control system is configured to keep the chips of biomass for a residence time of 8 to 20 minutes in the thermal hydrating stage, which is long enough to saturate the chips of biomass with moisture before moving the biomass to the steam explosion stage.

3. The integrated plant of claim 2,
where the thermal hydrating stage, via a screw feed system, feeds the chips of biomass that have been softened and increased in moisture content to the steam explosion stage, which is maintained by the control system to be at a pressure of 10 to 30 times atmospheric pressure, and where the steam explosion stage further raises the moisture content of the biomass and internal pressure of cells making up the biomass.

4. The integrated plant of claim 2,
where the steam explosion stage has a set of temperature and pressure sensors and a second control system,
where the biomass is exposed to high temperature and high pressure steam of at least 188 degrees C. and 160 PSI from the second steam supply input between 5 minutes to 20 minutes until moisture penetrates porous portions of a bulk structure of the biomass and all of the fluids and gases present in the biomass are raised to the high pressure,
where a conveyor system feeds the biomass through the steam explosion stage to the exit orifice,
where a small opening of the exit orifice goes into a tube that is maintained at reduced pressure of 4-10 bar, and where any internal fluids or gases at the high pressure expand to internally blow apart the bulk structure of the biomass into the moist fine particle form of biomass.

5. The integrated plant of claim 2,
where the steam explosion stage is configured for high pressure steam at greater than 14 bar and contains a discharge outlet configured to "explode" the biomass at a lower pressure to produce the biomass in the fine particle form,
where a magnetic filter and an air cleaning filter system couples to the thermal hydrating stage to ensure metal fragments and heavy rocks are removed from the chips of biomass prior to entering the thermal hydrating stage in order to prevent these metal fragments and heavy rocks from plugging portions of the steam explosion stage including the discharge outlet, and
where the biomass in the fine particle form flows through a feed line of a blow vessel at high velocity, and flow aids, including any of 1) flowable solids and 2) gases, are injected at any of 1) the discharge outlet of the steam explosion stage and 2) in the feed line to prevent clogs by the biomass, and, in addition, the feed line has heating coils traced around the feed line to maintain an elevated temperature of the biomass in the fine particle form to help prevent crystallization of rosins and resin acids in the biomass in the fine particle form.

6. The integrated plant of claim 2,
where after the thermal hydrating stage, the softened biomass in chip form is any combination of 1) crushed and 2) compressed into a plug form, which is then fed into a continuous screw conveyor system which moves the biomass in the plug form into the steam explosion stage,
where, in the continuous screw conveyor system, the biomass in the plug form prevents blowback backpressure from high pressure steam at at least fourteen times atmospheric pressure in the steam explosion stage from affecting the thermal hydrating stage, and
where syngas components including hydrogen ($H_2$) and carbon monoxide (CO) from the biomass gasifier are fed to a downstream methanol synthesis reactor to create methanol, which is also part of the integrated plant.

7. The integrated plant of claim 6,
where the steam explosion stage couples to a refiner stage that has one or more blades configured to mechanically agitate pressurized biomass prior to the pressurized biomass exiting the steam explosion stage through the exit orifice to a blow line maintained at a pressure of less than a third of the pressure inside the steam explosion stage in order to internally blow apart the pressurized biomass, and
where the mechanical agitation in the refiner stage is configured to cause resulting biomass in the particle form to have a more consistent average size distribution of biomass particles.

8. The integrated plant of claim 1,
where the two or more stages are of the steam explosion unit and include a thermal hydrating stage and a steam explosion stage,
where the thermal hydrating stage has a first set of temperature sensors and a control system configured to apply the steam via the first steam supply input to the chips of biomass at a temperature above a glass transition point of the lignin in order to soften and elevate the moisture content of the biomass so at least the cellulose fibers of the biomass in the steam explosion stage can be internally blown apart from the biomass,
where the thermal hydrating stage is configured to receive the chips of biomass formed from one or more sources of biomass selected from leaves, needles, bark, and trunk wood, and then the control system heats the chips of biomass in the thermal hydrating stage to greater than 60° C. using the steam for a residence of time of 8 to 20 minutes, and then sends the biomass to the steam explosion stage to create high pressure steam inside partially hollow cellulose fibers and other porous areas in a bulk structure of the biomass, and then an environmental pressure past the exit orifice of the steam explosion stage is dropped rapidly by extruding the bulk structure of the biomass maintained by the control system in the steam explosion stage to be between 160 to 450 PSI into a tube at less pressure to cause an internal explosion, which internally blows apart the biomass into minute fine particles of biomass, and
where internally blowing apart fiber bundles of the bulk structure of the biomass into pieces and fragments of cellulose fiber, lignin, and hemi-cellulose results in both 1) an increase of a surface area of the biomass in the fine particle form compared to the received chips of biomass, and 2) a change in structure of the biomass in the fine particle form configured to flow like grains of sand rather than like fibers.

9. The integrated plant of claim 1,
where the two or more stages are of the steam explosion unit and include a thermal hydrating stage and a steam explosion stage,
where at the exit orifice of the steam explosion stage, once the biomass explodes into the moist fine particle form, then particles of biomass lose a percentage of their moisture due to steam flashing in a blow line and being vented off as a water vapor,
where the produced particles of biomass and the moisture are then separated by a cyclone filter,
where the moisture of the particles of biomass is further removed at an exit of a blow vessel by a dryer that reduces a moisture content of the particles of biomass to less than 20% by weight, and
where the dryer then feeds the particles of biomass with their reduced moisture content to a silo for storage until ready to be fed into the biomass gasifier.

10. The integrated plant of claim 1,
where a steam explosion stage couples to a refiner stage that has one or more blades configured to mechanically agitate pressurized biomass prior to the pressurized biomass exiting the steam explosion stage through the exit orifice to a blow line, where the fine particle form of the biomass has reduced moisture content and includes cellulose fibers that are fragmented, torn, shredded, and any combination of these, and the particles of fine particle form of the biomass have an average dimension of less than 30 microns thick and less than 200 microns in length, and
where the the particles of the fine particle form of the biomass are fed downstream to the biomass gasifier for a rapid biomass gasification reaction in the reactor vessel of the biomass gasifier because they create a higher surface to volume ratio for the same amount of biomass compared to the received chips of biomass, which allows a higher heat and mass transfer to the biomass and a more rapid thermal decomposition and gasification of all the molecules in the biomass.

11. The integrated plant of claim 1, further comprising:
a water separation unit,
where a collection chamber at an outlet stage of the steam explosion stage is used to collect the biomass reduced into smaller particle sizes and in pulp form for feeding to the water separation unit,
where water is removed from the biomass in the fine particle form in a cyclone unit for feeding the biomass to a dryer to further reduce moisture content of the biomass in the fine particle form to less than 20% by weight; and
where gases containing organic compounds coming out of the steam explosion stage that are recovered from the cyclone unit are collected for feeding through a feedline to the biomass gasifier.

* * * * *